US008410140B2

(12) United States Patent
Brummett

(10) Patent No.: US 8,410,140 B2
(45) Date of Patent: Apr. 2, 2013

(54) ANESTHETIC METHODS AND COMPOSITIONS

(75) Inventor: Chad M. Brummett, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 202 days.

(21) Appl. No.: 12/791,506

(22) Filed: Jun. 1, 2010

(65) Prior Publication Data

US 2010/0305160 A1     Dec. 2, 2010

Related U.S. Application Data

(60) Provisional application No. 61/182,924, filed on Jun. 1, 2009.

(51) Int. Cl.
*A61K 31/445*     (2006.01)
(52) U.S. Cl. ........................................ 514/330
(58) Field of Classification Search .................. None
See application file for complete search history.

(56) References Cited

PUBLICATIONS

Brummett et al (Reg Anesth Pain Med 30(3):A55, 2005).*
Phan et al (Paediatr Drugs 10:49-69, 2008—abstract only).*
Graf et al (Anesthesiology 96:1427-1434, 2002).*
Slingsby et al (J Vet Pharmacol Ther 31:135-142, 2008).*
Allison (1995) in Survival Analysis Using SAS: A Practical Guide, ed. by PD Allison, ND Cary, SAS Publishing, "Estimating Cox Regression Models With PROC PHREG," pp. 111-134.
Auroy et al. "Major Complications of Regional Anesthesia in France," (2002) Anesthesiol. 97:1274-80.
Bonafide et al. "Remifentanil Inhibits Rapid Eye Movement Sleep but Not the Nocturnal Melatonin Surge in Humans," (2008) Anesthesiol. 108:627-633.
Bowdle, "Nocturnal Arterial Oxygen Desaturation and Episodic Airway Obstruction After Ambulatory Surgery," (2004) Anesth. Analg. 99:70-76.
Brull et al. "Neurological Complications After Regional Anesthesia: Contemporary Estimates of Risk," (2007) Anesth. Analg. 104:965-74.
Brummett et al. "Perineural Administration of Dexmedetomidine in Combination with Bupivacaine Enhances Sensory and Motor Blockade in Sciatic Nerve Block without Inducing Neurotoxicity in Rat," (2008) Anesthesiol. 109:502-511.
Butterworth et al., "The α2-Adrenergic Agonists Clonidine and Guanfacine Produce Tonic and Phasic Block of Conduction in Rat Sciatic Nerve Fibers," (1993) Anesth. Analg. 76:295-301.
Candido et al., "Neurologic Sequelae After Interscalene Brachial Plexus Block for Shoulder/Upper Arm Surgery: The Association of Patient, Anesthetic, and Surgical Factors to the Incidence and Clinical Course," (2005) Anesth. Analg. 100:1489-95.
Carollo et al., "Dexmedetomidine: a review of clinical applications," (2008) Curr. Opin. Anaesthesiol. 21:457-461.
Casati et al., "Small-Dose Clonidine Prolongs Postoperative Analgesia After Sciatic-Femoral Nerve Block with 0.75% Ropivacaine for Foot Surgery," (2000) Anesth. Analg. 91:388-92.
Casati et al., "Interscalene brachial plexus anesthesia with either 0.5% ropivacaine or 0.5% bupivacaine," (2000) Minerva Anesesiol. 66:39-44.
Chazalon et al., "Ropivacaine-induced Cardiac Arrest after Peripheral Nerve Block: Successful Resuscitation," (2003) Anesthesiol. 99:1449-1451.
Cucchiaro et al., "The Effects of Clonidine on Postoperative Analgesia After Peripheral Nerve Blockade in Children," (2007) Anesth. Analg. 104:532-537.
Culebras et al., "Clonidine Combined with a Long Acting Local Anesthetic Does Not Prolong Postoperative Analgesia after Brachial Plexus Block but Does Induce Hemodynamic Changes," (2001) Anesth. Analg. 92:199-204.
Dalle et al., "Inhibition of The Ih Current in Isolated Peripheral Nerve: A Novel Mode of Peripheral Antinociception?," (2001) Muscle Nerve 24:254-261.
Dirig et al., "Characterization of variables defining hindpaw withdrawal latency evoked by radiant thermal stimuli," (1997) Neurosci. Methods 76:183-191.
Dobrydnjov et al., "Postoperative pain relief following intrathecal bupivacaine combined with intrathecal or oral clonidine," (2002) Anaesthiol. Scand. 46:806-814.
Dyhre et al., "Local Anesthetics in Lipid-Depot Formulations—Neurotoxicity in Relation to Duration of Effect in a Rat Model," (2006) Reg. Anesth. Pain Med. 31:401-408.
Dyhre et al., "The duration of ropivacaine and in the rat action of bupivacaine, levobupivacaine, Dethidine in DeriDheral nerve block," ( 1997) Acta Anaesthiol. Scand. 41:1346-1352.
Eisenach et al., "Alpha sub 2 -Adrenergic Agonists for Regional Anesthesia: a Clinical Review of Clonidine (1984-1995)," (1996) Anesthesiol. 85:655-674.
El Saied et al., "Clonidine prolongs the effect of ropivacaine for axillary brachial plexus blockade," (2000) Can. J. Anaesth.47:962-967.
Eledjam et al., "Brachial plexus block with bupivacaine: effects of added alphaadrenergic agonists: comparison between clonidine and epinephrine," (1991) Can. J. Anaesth. 38:870-875.
Erlacher et al., "The effects of clonidine on ropivacaine 0.75% in axillary perivascular brachial plexus block," (2000) Acta Anaesthesiol. Scand. 44:53-57.
Gaumann et al., "Comparison Between Clonidine and Epinephrine Admixture to Lidocaine in Brachial Plexus Block," (1992) Anesth. Analg. 75:69-74.
Gaumann et al., "Clonidine Enhances the Effects of Lidocaine on C-Fiber Action Potential," (1992) Anesth. Analg.74:719-725.
Gaumann et al., "Hyperpolarizing Afterpotentials in C Fibers and Local Anesthetic Effects of Clonidine and Lidocaine," (1994) Pharmacol.48:21-29.
Gentili et al., "Clinical and Experimental Aspects of Injection Injuries of Peripheral Nerves," (1980) Can. J Neurol. Sci. 7:143-51.

(Continued)

*Primary Examiner* — Craig Ricci
(74) *Attorney, Agent, or Firm* — Casimir Jones

(57) ABSTRACT

The present invention relates to compositions and methods use in pain reduction, including but not limited to, peripheral nerve blocks. In particular, the present invention relates to compositions and methods for the administration of perineural dexmedetomidine and ropivacaine in combination for increased antinociception in peripheral nerve blocks. In addition, this invention relates to any use of dexmedetomidine alone or in combination with other agents for the purpose of decreasing inflammation around peripheral nerves, thereby decreasing the potential for peripheral nerve injury. Further, the invention relates to the use of dexmedetomidine to reduce inflammation in the muscle to lessen or prevent muscle damage.

6 Claims, 27 Drawing Sheets

PUBLICATIONS

Gerner et al., "Differential Block of N-Propyl Derivatives of Amitriptyline and Doxepin for Sciatic Nerve Block in Rats," (2005) Reg. Anesth. Pain Med. 30:344-350.

Hadzic et al., "Combination of Intraneural Injection and High Injection Pressure Leads to Fascicular Injury and Neurologic Deficits in Dogs," (2004) Reg. Anesth. Pain Med. 29:417-23.

Hansen, "Ropivacaine: a pharmacological review," (2004) Expert Rev. Neurother.4:781-791.

Hargreaves et al., A new and sensitive method for measuring thermal nociception in cutaneous hyperalgesia, (1988) Pain 32:77-88.

Hebl, "Ultrasound-guided Regional Anesthesia and the Prevention of Neurologic Injury," (2008) Anesthesiol. 108:186-8.

Hickey et al., "A Comparison of Ropivacaine 0.5% and Bupivacaine 0.5% for Brachial Plexus Block," (1991) Anesthesiol 74:639-642.

Hickey et al., "A Comparative Study of 0.25% Ropivacaine and 0.25% Bupivacaine for Brachial Plexus Block," (1992) Anesth Analg 75:602-606.

Hung et al., "Ephedrine Blocks Rat Sciatic Nerve in Vivo and Sodium Channels in Vitro," (2005) Anesthsiol. 103:1246-1252.

Hutschala et al., "Clonidine added to bupivacaine enhances and prolongs analgesia after brachial plexus block via a local mechanism in healthy volunteers," (2004) Eur. J. Anaesthesiol. 21:198-204.

Iohom et al., "The Effects of Clonidine Added to Mepivacaine for Paronychia Surgery Under Axillary Brachial Plexus Block," (2005) Anesth. Analg. 100:1179-1183.

Iskandar et al., "The Enhancement of Sensory Blockade by Clonidine Selectively Added to Mepivacaine After Midhumeral Block," (2001) Anesth. Analg. 93:771-775.

Iskandar et al., "The Analgesic Effect of Interscalene Block Using Clonidine as an Analgesic for Shoulder Arthroscopy," (2003) Anesth. Analg. 96:260-262.

Kapur et al., "Neurologic and histologic outcome after intraneural injections of lidocaine in canine sciatic nerves," (2007) Acta Anaesthesiol. Scand. 51:101-7.

Kau et al., "Efficacy of Lidocaine or Bupivacaine Combined With Ephedrine in Rat Sciatic Nerve Block," (2006) Reg. Anesth. Pain Med. 31:14-18.

Khoo et al., "Successful Resuscitation of an ASA 3 patient Following Ropivacaine-induced Cardiac Arrest," (2006) Anaesth. Intensive Care 34:804-807.

Klein et al., "Successful Resuscitation After Ropivacaine-Induced Ventricular Fibrillation," (2003) Anesth. Analg. 97:901-903.

Kroin et al., "Clonidine Prolongation of Lidocaine Analgesia after Sciatic Nerve Block in Rats Is Mediated via the Hyperpolarization-activated Cation Current, Not by -Adrenoreceptors," (2004) Anesthesiol. 101:488-494.

Kytta et al., "Effects of repeated bupivacaine administration on sciatic nerve and surrounding muscle tissue in rats," (1986) Acta Anaesthesiol. Scand. 30:625-629.

Lavand'Homme et al., "Perineural 2A-Adrenoceptor Activation Inhibits Spinal Cord Neuroplasticity and Tactile Allodynia after Nerve Injury," (2002) Anesthesiol. 97(4):972-80.

Lavand'Homme et al., "Perioperative administration of the a2-adrenoceptor agonist clonidine at the site of nerve injury reduces the development of mechanical hypersensitivity and modulates local cytokine expression," (2003) Pain 105:247-54.

Litz et al., "Successful resuscitation of a patient with ropivacaine-induced asystole after axillary plexus block using lipid infusion," (2006) Anesthesia 61:800-801.

Liu et al., "Perineural clonidine reduces p38 mitogen-activated protein kinase activation in sensory neurons," (2006) Neuroreport. 17(12):1313-7.

Lydic et al., in Sleep and Pain, ed. by G. Lavigne, BJ Sessle, M Choinire M, PJ Soja, "Neurochemical Mechanisms Mediating Opioid-Induced REM Sleep Disruption," (2007) IASP Press, Seattle, WA pp. 99-122.

Martin et al., "The Role of the α2-Adrenoceptor Agonist Dexmedetomidine in Postsurgical Sedation in the Intensive Care Unit," (2003) J. Intensive Care med. 18:29-41.

Obayah et al., "Addition of dexmedetomidine to bupivacaine for greater palatine nerve block prolongs postoperative analgesia after cleft palate repair," (2010) European J Anaesthesiology 27 (3):280-284.

Ohmura et al., "Systemic Toxicity and Resuscitation in Bupivacaine-, Levobupivacaine-, or Ropivacaine-Infused Rats," (2001) Anesth. Analg. 93:743-748.

Ota et al., "Prolongation of Tetracaine Spinal Anesthesia by Oral Clonidine," (1992) Anesth. Analg. 75:262-264.

Pape, "Queer Current and Pacemaker: The Hyperpolarization-Activated Cation Current in Neurons," (1996) Ann. Rev. Physiol. 58:299-327.

Pere et al., "Local Myotoxicity of Bupivacaine in Rabbits After Continuous Supraclavicular Brachial Plexus Block," (1993) Reg. Anesth. 18:304-7.

Polley et al., "Ropivacaine and Bupivacaine: Concentrating on Dosing!," (2003) Anesth. Analg. 96:1251-1253.

Polley et al., "Cardiac Arrest following Regional Anesthesia with Ropivacaine," (2003) Anesthesiol. 99:1253-1254.

Ramsay et al., "Dexmedetomidine as a Total Intravenous Anesthetic Agent," (2004) Anesthesiol.101:787-790.

Ramsay et al., "Tracheal resection in the morbidly obese patient: the role of dexmedetomidine," (2006) J. Clin. Anesth.18:452-454.

Reinhart et al., "Postoperative Analgesia After Peripheral Nerve Block for Podiatric Surgery: Clinical Efficacy and Chemical Stability of Lidocaine Alone Versus Lidocaine Plus Clonidine," (1996) Anesth. Analg. 83:760-765.

Remington's Pharmaceutical Sciences, Mack Publishing Co. (A. R. Gennaro edit. 1985).

Romero-Sandoval et al., "2-Adrenoceptor Stimulation Transforms Immune Responses in Neuritis and Blocks Neuritis-Induced Pain," (2005) J. Neurosci. 25:8988-8994.

Romero-Sandoval et al., "Perineural Clonidine Reduces Mechanical Hypersensitivity and Cytokine Production in Established Nerve Injury," (2006) Anesthesiol. 104:351-355.

Romero-Sandoval et al., "Clonidine reduces hypersensitivity and alters the balance of pro- and anti-inXammatory leukocytes after local injection at the site of inXammatory neuritis," (2007) Brain Behav. Immun. 21:569-580.

Rosenberg et al., "Post-operative sleep disturbance: casuse, factors and effects on outcome," (1995) Eur. J. Anaesthesiol. Suppl. 10:28-30.

Sia et al., "Clonidine Administered as an Axillary Block Does Not Affect Postoperative Pain When Given as the Sole Analgesic," (1999) Anesth. Analg. 88:1109-1112.

Siegel et al., "Needlestick Distal Nerve Injury in Rats Models Symptoms of Complex Regional Pain Syndrome," (2007) Anesth. Analg. 105:1820-9.

Simpson et al., "Ropivacaine A Review of its Use in Regional Anaesthesia and Acute Pain Management," (2005) Drugs 65:2675-2717.

Singelyn et al., "Adding Clonidine to Mepivacaine Prolongs the Duration of Anesthesia and Analgesia after Axillary Brachial Plexus block," (1992) Reg. Anesth. 17:148-150.

Singelyn et al., "A Minimum Dose of Clonidine Added to Mepivacaine Prolongs the Duration of Anesthesia and Analgesia After Axillary Brachial Plexus Block," (1996) Anesth Analg 83:1046-1050.

Soderberg et al., "Ultralong Peripheral Nerve Block by Lidocaine:Prilocaine 1:1 Mixture in a Lipid Depot Formulation," (2006) Anesthiol. 104:110-121.

Starke et al., "Adrenergic Neuron Blockade by Clonidine: Comparison With Guanethidine and Local Anesthetics," (1972) Arch. Int. Pharmacodyn. Ther. 195:291-308.

Vaghadia et al., "A multicentre trial of ropivacaine 7.5 mg.m1-1 vs bupivacaine 5 mg.m1-1 for supra clavicular brachial plexus anesthesia," (1999) Can J. Anaesth. 46:946-951.

Venn et al., "A multicentre trial of ropivacaine 7.5 mg.m1-1 vs bupivacaine 5 mg.m1-1 for supra clavicular brachial plexus anesthesia," (2001) Br. J. Anaesth. 87:684-690.

Voelckel et al., "Signs of Inflammation After Sciatic Nerve Block in Pigs," (2005) Anesth .Analg. 101:1844-6.

Yaksh et al., "Reversal of Nerve Ligation-Induced Allodynia by Spinal Alpha- 2 Adrenoceptor Agonists1," (1995) J. Pharmacol. Exp. Ther. 272:207-214.

Zink et al., "Benefit-Risk Assessment of Ropivacaine in the Management of Postoperative Pain," (2004) Drug Saf. 27:1093-1114.

\* cited by examiner

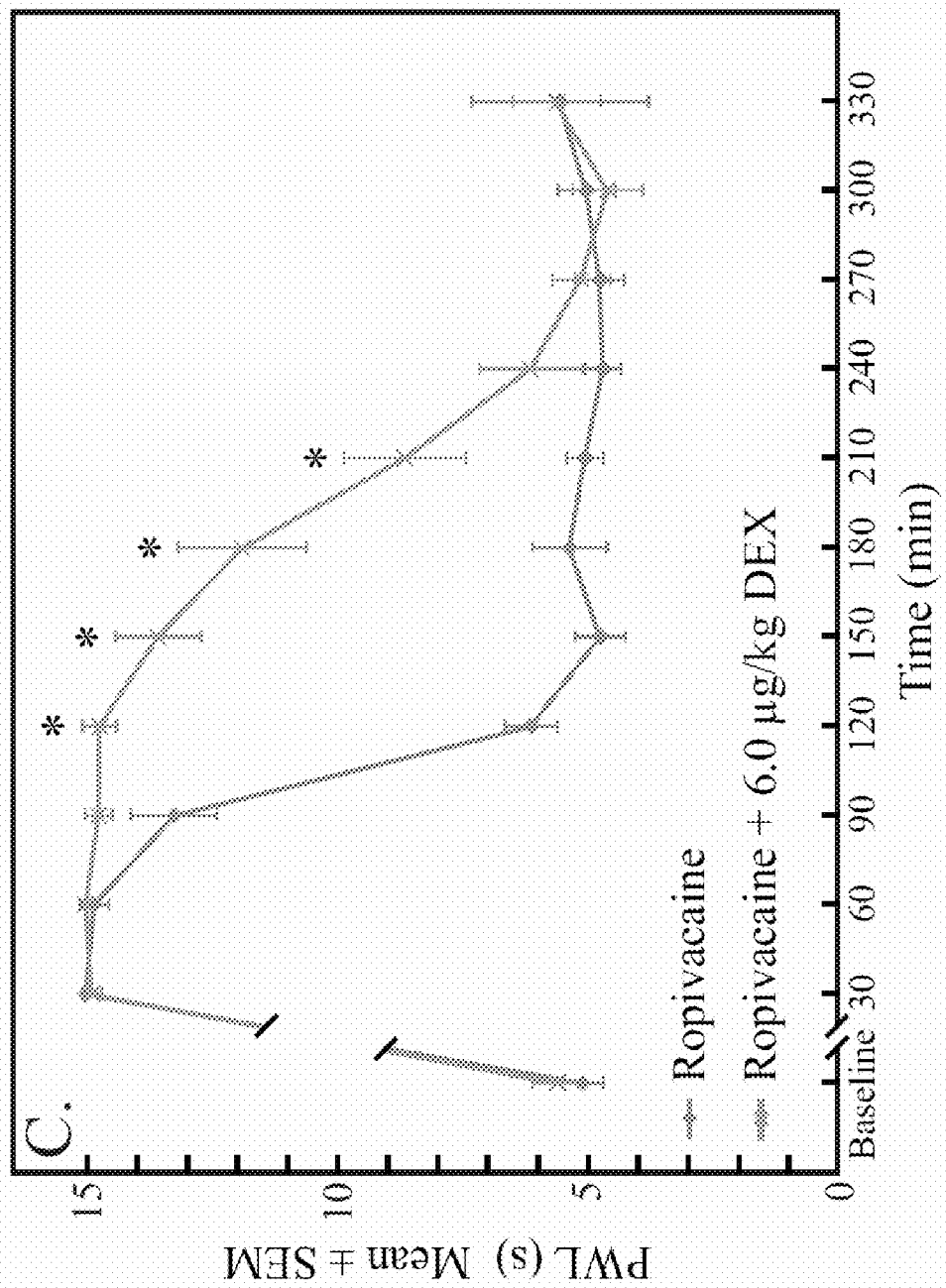

ANESTHETIC METHODS AND COMPOSITIONS

CROSS REFERENCE TO RELATED APPLICATIONS

This Application claims priority to U.S. Provisional Patent Application Ser. No. 61/182,924, filed Jun. 1, 2009, hereby incorporated by reference in its entirety.

STATEMENT REGARDING FEDERALLY SPONSORED RESEARCH OR DEVELOPMENT

This invention was made with government support under RR024986 and HL040881 awarded by the National Institutes of Health. The government has certain rights in the invention.

FIELD OF THE INVENTION

The present invention relates to compositions and methods use in pain reduction, including but not limited to, peripheral nerve blocks. In particular, the present invention relates to the administration of perineural dexmedetomidine and ropivacaine in combination for increased antinociception in peripheral nerve blocks. In addition, this invention relates to any use of dexmedetomidine alone or in combination with other agents for the purpose of decreasing inflammation around peripheral nerves, thereby decreasing the potential for peripheral nerve injury. Further, the invention relates to the use of dexmedetomidine to reduce inflammation in the muscle to lessen or prevent muscle damage.

BACKGROUND OF THE INVENTION

The prevention of pain is a critical component of medical practice, whether it is needed for the alleviation of endemic pain due to disease, injury, or other conditions, or to enable medical or surgical procedures. Among the variety of anesthetic methods currently used in modern medicine, some methods allow regional or local pain relief or numbness, either in absence or presence of patient sedation or consciousness. Peripheral nerve blocks may be used for nerves outside of the central nervous system, and find particular use in outpatient surgical settings. However, peripheral nerve blocks pose particular problems in terms of safety and effective duration; that is, drugs and dosages that are found to be effective and safe when applied to nerves of the central nervous system (e.g., during epidural injection) do not predictably have the same systemic toxicity, neurotoxicity, and effectiveness when applied to peripheral nerve blocks. Therefore, there is a need for safer, longer-lasting, and more effective anesthetic and analgesic compositions and methods for peripheral nerve blocks.

SUMMARY OF THE INVENTION

The present invention relates to compositions and methods for reducing pain, including but not limited to, methods and compositions for peripheral nerve blocks. In particular, the present invention relates to the administration of perineural dexmedetomidine and ropivacaine in combination for increased antinociception in peripheral nerve blocks. In addition, this invention relates to any use of dexmedetomidine alone or in combination with other agents for the purpose of decreasing inflammation around peripheral nerves, thereby decreasing the potential for peripheral nerve injury. Further, the invention relates to the use of dexmedetomidine to reduce inflammation in the muscle to lessen or prevent muscle damage. Types of nerve injury include but are not limited to direct needle trauma, compression, hematoma, local anesthetic toxicity, surgical trauma, and stretch injury. Types of muscle damage include but are not limited to direct needle trauma, compression, hematoma, local anesthetic toxicity, surgical trauma, and stretch injury.

In certain embodiments, methods and compositions of the present invention relates to regional or peripheral nerve blocks. Types of regional or peripheral nerve blocks include but are not limited to motor nerve blocks, sensory nerve blocks, differential nerve blocks, autonomic nerve blocks, brachial plexus nerve blocks (axillary, interscalene, supraclavicular, infraclavicular), individual upper extremity nerve blocks (median, radial, ulnar, musculocutaneous, axillary), sciatic nerve blocks, ankle nerve blocks, metatarsal nerve blocks, oral nerve blocks, femoral nerve blocks, popliteal fossa nerve blocks, saphenous nerve blocks, distal nerve blocks, digital nerve blocks, deep peroneal nerve blocks, superficial peroneal nerve blocks, tibial nerve blocks, sural nerve blocks, and saphenous nerve blocks.

In certain embodiments, the invention provides methods and compositions for reducing pain, comprising administering an $\alpha_2$-adrenoceptor agonist in combination with a long-acting local anesthetic. In certain embodiments, additional agents are used.

Methods and compositions of the present invention are not limited by the route of delivery or routes of administration by which therapeutic agents are administered. Routes of delivery include but are not limited to single injection, serial injections, indwelling catheter, continuous infusion, transdermal, and transmucosal administration. Routes of administration include but are not limited to intravenous, subcutaneous, intraperitoneal, inhalation, oral, intrapulmonary, transdermal, transmucosal, and intramuscular.

The methods and compositions of certain embodiments of the present invention find use in treating many types of pain. Methods and compositions of certain embodiments of the present invention may be used to treat existing pain (e.g. pain associated with an injury, previously performed medical procedure, or pathological condition), or for the prevention of pain (e.g., prior to or during a surgical or other medical procedure). Types of pain include but are not limited to acute pain, chronic pain, thermal pain, traumatic pain, chemical pain, inflammatory pain, ischemic pain, blunt pain, sharp pain, prickling pain, visceral pain, and neuropathic pain. Furthermore, methods and compositions of certain embodiments of the present invention find use in treating subjects of various types. Methods and compositions of the present invention may be used in a variety of settings including but not limited to human medical (e.g., clinical, emergency, search-and-rescue), veterinary (e.g., for companion animal subjects, for livestock subjects, for wildlife subjects), or research (e.g., for research animals). Subjects include but are not limited to dogs, cats, rats, mice, rabbits, horses, bovines, goats, pigs, primates, and humans. In preferred embodiments, the subject is a human. The human subject may have an underlying or additional condition. Such conditions may include but are not limited to advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and impaired tolerance of anesthetic and/or analgesic agents (e.g., due to genetic predisposition or metabolic condition).

In certain embodiments, the present invention provides kits for use with methods or compositions for reduction of pain in a subject. In preferred embodiments, the subject is a human. In some embodiments, the kit provides, a composition for reduction of pain. In some embodiments, the kit further comprises components that include but are not limited to compositions described herein, syringes, stimulating needles, antiseptic wipes or solutions, sedative agent(s), labels, written and/or pictorial instructions and product information, and package environmental controls (e.g., ice, desiccants, etc).

In certain embodiments, the present invention provides a method for reducing pain in a subject, comprising administering an $\alpha_2$-adrenoceptor agonist in combination with a long-acting local anesthetic as a peripheral nerve block. In some embodiments, the $\alpha_2$-agonist is dexmedetomidine. In some embodiments, the long-acting local anesthetic is an agent such as bupivacaine, levobupivacaine, and ropivacine. In some embodiments, the long-acting local anesthetic is ropivacaine. In some embodiments, the dose of dexmedatomidine is 5 µg/kg or less. The dose may be less than 0.1 µg/kg, 0.1-0.2 µg/kg, 0.2-0.3 µg/kg, 0.3-0.4 µg/kg, 0.4-0.5 µg/kg, 0.5-0.6 µg/kg, 0.6-0.7 µg/kg, 0.7-0.8 µg/kg, 0.8-0.9 µg/kg, 0.9-1 µg/kg, 1-2 µg/kg, 2-4 µg/kg, 4-6 µg/kg, 6-8 µg/kg, 8-10 µg/kg, 10-20 µg/kg or more. In some embodiments, the dose of ropivacaine is 1.0% or less. The dose of ropivacaine may be less than 0.1%, 0.1-0.2%, 0.2-0.3%, 0.3-0.4%, 0.4-0.5%, 0.5-0.75%, 0.75-1.0%, 1.0-5.0%, 5.0-10.0%, 10.0% or more. In some embodiments, the addition of an $\alpha_2$-adrenoceptor agonist permits a lower dose of local anesthetic than would be used in the absence of the $\alpha_2$-adrenoceptor agonist (e.g., lower dose than clinically recommended doses by 50%, two-fold, three-fold, four-fold, etc.) In doing so, toxicity associated with the local anesthetic may be reduced or eliminated.

In some embodiments, the subject is a human. In some embodiments, the human subject has an additional condition such as advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and impaired tolerance of anesthetic or analgesic agents.

In some embodiments, the peripheral nerve block is a type such as a motor nerve block, a sensory nerve block, a differential nerve block, an autonomic nerve block, a brachial plexus nerve block (axillary, interscalene, supraclavicular, infraclavicular), an individual upper extremity nerve block (median, radial, ulnar, musculocutaneous, axillary), a sciatic nerve block, ankle nerve block, metatarsal nerve block, oral nerve block, femoral nerve block, popliteal fossa nerve block, saphenous nerve block, distal nerve block, digital nerve block, deep peroneal nerve block, superficial peroneal nerve block, tibial nerve block, sural nerve block, or saphenous nerve block. In some embodiments, more than one peripheral nerve block is performed. In some embodiments, the delivery route may be a single injection, serial injections, indwelling catheter, continuous infusion, transdermal administration, and/or transmucosal administration. In some embodiments, the route of administration is a type such as intravenous, subcutaneous, intraperitoneal, inhalation, oral, intrapulmonary, transdermal, transmucosal, and/or intramuscular. In some embodiments, the type of pain includes but is not limited to acute pain, chronic pain, thermal pain, traumatic pain, chemical pain, inflammatory pain, ischemic pain, blunt pain, sharp pain, prickling pain, visceral pain, and/or neuropathic pain.

In certain embodiments, the present invention provides a method for reducing pain in a subject comprising administration of dexmedetomidine in combination with ropivacaine to a peripheral nerve. In some embodiments, the dose of dexmedatomidine is 5 µg/kg or less. The dose may be less than 0.1 µg/kg, 0.2 µg/kg, 0.3 µg/kg, 0.4 µg/kg, 0.5 µg/kg, 0.6 µg/kg, 0.7 µg/kg, 0.8 µg/kg, 0.9 µg/kg, 1 µg/kg, 1-2 µg/kg, 2-4 µg/kg, 4-6 µg/kg, 6-8 µg/kg, 8-10 µg/kg, 10-20 µg/kg or more. In some embodiments, the dose of ropivacaine is 1.0% or less. The dose of ropivacaine may be less than 0.1%, 0.1%-0.2%, 0.2%-0.3%, 0.3%-0.4%, 0.4-0.5%, 0.5-0.75%, 0.75-1.0%, 1.0-5.0%, 5.0-10.0%, 10.0% or more. In some embodiments, the subject is a human. In some embodiments, the human subject has an additional condition such as advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and/or impaired tolerance of anesthetic or analgesic agents. In some embodiments, the type of peripheral nerve block is a motor nerve block, a sensory nerve block, a differential nerve block, an autonomic nerve block, a brachial plexus nerve block (axillary, interscalene, supraclavicular, infraclavicular), an individual upper extremity nerve block (median, radial, ulnar, musculocutaneous, axillary), a sciatic nerve block, ankle nerve block, metatarsal nerve block, oral nerve block, femoral nerve block, popliteal fossa nerve block, saphenous nerve block, distal nerve block, digital nerve block, deep peroneal nerve block, superficial peroneal nerve block, tibial nerve block, sural nerve block, or saphenous nerve block. In some embodiments, more than one peripheral nerve block is performed. In some embodiments, the delivery route is a single injection, serial injections, indwelling catheter, continuous infusion, transdermal administration, and/or transmucosal administration.

In certain embodiments, the present invention provides a composition for antinociception in a subject comprising dexmedatomidine in combination with ropivacaine. In some embodiments, the composition is configured for administration of a peripheral nerve block. In some embodiments, the formulation of the composition is configured to deliver a dose of dexmedatomidine of 5 µg/kg or less. The dose may be less than 0.1 µg/kg, 0.1-0.2 µg/kg, 0.2-0.3 µg/kg, 0.3-0.4 µg/kg, 0.4-0.5 µg/kg, 0.5-0.6 µg/kg, 0.6-0.7 µg/kg, 0.7-0.8 µg/kg, 0.8-0.9 µg/kg, 0.9-1 µg/kg, 1 µg/kg, 1-2 µg/kg, 2-4 µg/kg, 4-6 µg/kg, 6-8 µg/kg, 8-10 µg/kg, 10-20 µg/kg or more. In some embodiments, the formulation of the composition is configured to deliver a dose of ropivacaine of 1.0% or less. The dose of ropivacaine may be less than 0.1%, 0.1-0.2%, 0.2-0.3%, 0.3-0.4%, 0.4-0.5%, 0.5-0.75%, 0.75-1.0%, 1.0-5.0%, 5.0-10.0%, 10.0% or more. In some embodiments, the subject is a human. In some embodiments, the human subject has an additional condition such as advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and impaired tolerance of anesthetic or analgesic agents. In some embodiments, the type of peripheral nerve block is a motor nerve block, a sensory nerve block, a differential nerve block, an autonomic nerve block, a brachial plexus nerve block (axillary, interscalene, supraclavicular, infraclavicular), an individual upper extremity nerve block (median, radial, ulnar, musculocutaneous, axillary), a sciatic nerve block, ankle nerve block, metatarsal nerve block, oral nerve block, femoral nerve block, popliteal fossa nerve block, saphenous nerve block, distal nerve block, digital nerve block, deep peroneal nerve block, superficial peroneal nerve block, tibial nerve block, sural nerve block, or saphenous nerve block. In some embodiments, the composition is used to perform more than one peripheral nerve block. In some embodiments, the composition is formulated for a delivery route such as single injection, serial injection, indwelling catheter, continuous infusion, transdermal administration, and/or transmucosal administration.

Additional embodiments will be apparent to persons skilled in the relevant art based on the teachings contained herein.

DESCRIPTION OF THE FIGURES

FIG. 7D versus 7E). The drug condition for each group is noted in the bottom left corner (Nerve=drug injected perineurally; SQ=drug injected subcutaneously). The dose of dexmedetomidine was the same for the four groups with dexmedetomidine, and all groups with ropivacaine were maintained at 0.5%. DEX=dexmedetomidine; * indicates statistically significant result ($p<0.05$).

DEFINITIONS

Figure 1:
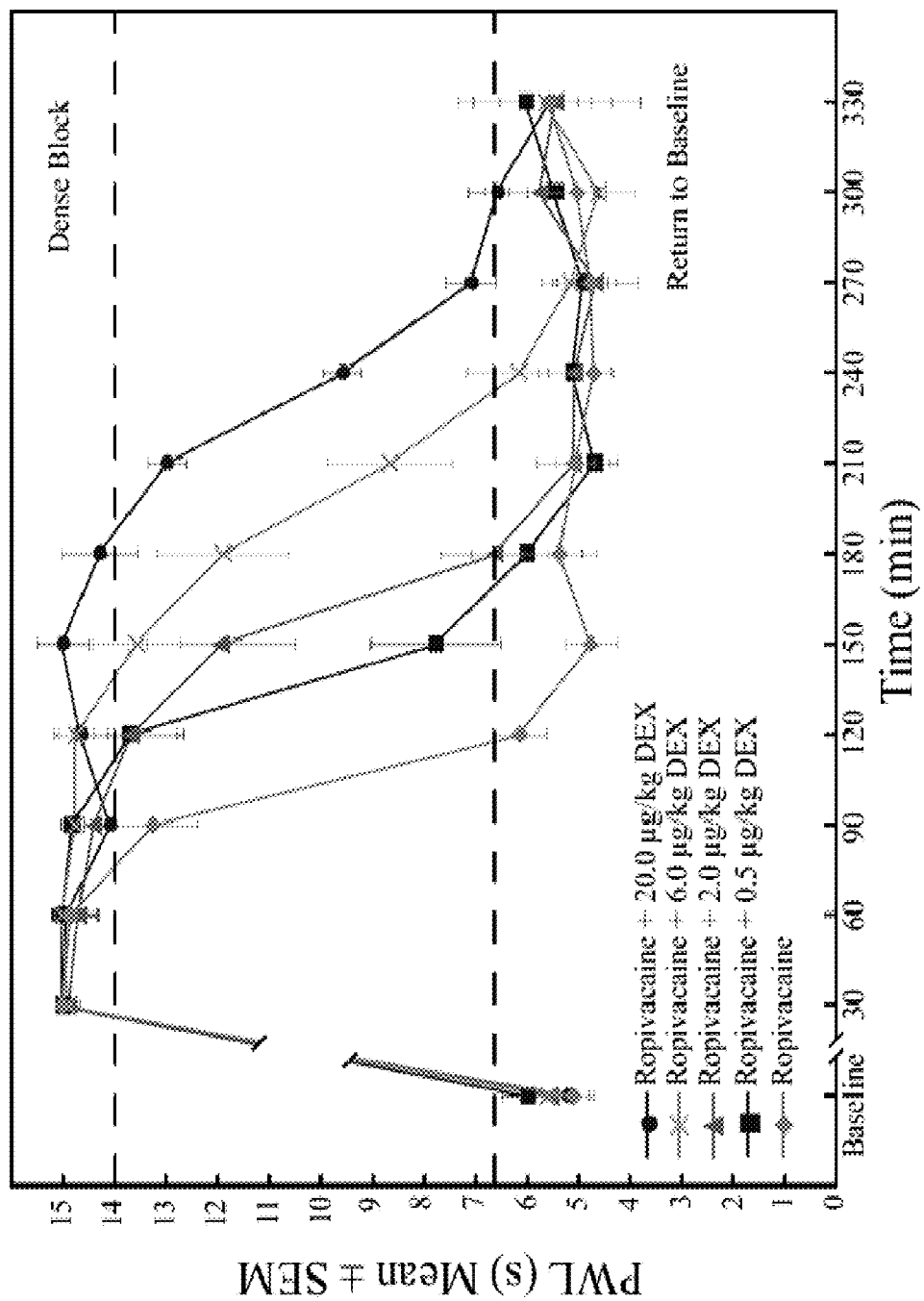
FIG. 1 shows that addition of dexmedetomidine (DEX) to ropivacaine enhanced the duration of dense sensory blockade ($p<0.001$) and time to return to normal sensory function ($p<0.001$) in response to a thermal stimulus in a dose-dependent fashion when compared to the control group, ropivacaine alone. The graph shows the time-course of paw withdrawal latency values of the baseline taken 24 hours before surgery (Baseline; mean value of all rats=$5.46\pm1.13$ seconds) and at 30-minute time-points after the sciatic nerve block.

To facilitate an understanding of the present invention, a number of terms and phrases are defined below:

As used herein, the term "$\alpha_2$-agonist" means an agent that selectively stimulates alpha adrenergic receptors. Such drugs may provide sedation, analgesia, muscle relaxation and anxiolysis. Types of $\alpha_2$-agonists include but are not limited to clonidine, romifidine, detomidine, dexmedetomidine, xylazine and medetomidine.

As used herein, the term "long-acting local anesthetic" means an agent that provides analgesia for, typically, 8-16 hours after a peripheral nerve block.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "condition" refers to any physiological status experienced by a subject. The condition may or may not be pathological. Examples of conditions include but are not limited to advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and impaired tolerance of anesthetic or analgesic agents (e.g., due to genetic predisposition, due to metabolic condition).

As used herein, the term "peripheral nerve block" refers to the introduction of an agent near or in a peripheral nerve for the reduction of pain or to provide numbness. Types of peripheral nerve blocks include but are not limited to motor, sensory, differential, and autonomic blocks, and additionally, include but are not limited to brachial plexus (axillary, interscalene, supraclavicular, infraclavicular), individual upper extremity nerve blocks (median, radial, ulnar, musculocutaneous, axillary), sciatic, ankle, metatarsal, oral, femoral, popliteal fossa, saphenous, distal, digital, deep peroneal, superficial peroneal, tibial, sural, and saphenous blocks.

As used herein, "prolonged nerve block" means prolonged pain relief or numbness. The duration of the pain relief or numbness may be 60-90 minutes, 90-120 minutes, 120-150 minutes, 150-180 minutes, 3-6 hours, 6-9 hours, 9-12 hours, 12-14 hours, 14-16 hours, 16-18 hours, 18-24 hours, 24-30 hours, 30-36 hours, 36 hours or more. In preferred embodiments, the duration of pain relief or numbness is 24 hours or more.

As used herein, the term "delivery route" refers to a method of introduction of a therapeutic agent into the body a subject. Delivery routes include but are not limited to single injection, serial injection, indwelling catheter, continuous infusion, transdermal administration, and transmucosal administration.

As used herein, the term "route of administration" refers to the path by which an agent is brought into contact with the body of a subject. Routes of administration include but are not limited to intravenous, subcutaneous, intraperitoneal, inhalation, oral, intrapulmonary, transdermal, transmucosal, and intramuscular.

As used herein, the term "pain" means a physiologic and/or psychologic reaction or response to potential or actual stimulus that may result in tissue damage, injury, disease, or other condition(s). Types of pain include but are not limited to acute pain, chronic pain, thermal pain, traumatic pain, chemical pain, inflammatory pain, ischemic pain, blunt pain, sharp pain, prickling pain, visceral pain, and neuropathic pain.

As used herein, the term "antinociception" means reduction in sensitivity to or perception of painful stimuli, without limitation to the type or nature of pain or the manner in which it is imparted.

As used herein, the term "nerve injury" includes but is not limited to direct needle trauma, compression, hematoma, local anesthetic toxicity, surgical trauma, and stretch injury.

As used herein, the term "muscle damage" includes but is not limited to direct needle trauma, compression, hematoma, local anesthetic toxicity, surgical trauma, and stretch injury.

DETAILED DESCRIPTION OF THE INVENTION

Peripheral nerve blocks are used frequently in a variety of surgical procedures for surgical anesthesia and postoperative pain. Long-acting local anesthetics alone can provide analgesia for 9-14 hours (Casati et al. (2000) *Minerva Anesesiol.* 66:39-44; Hickey et al. (1991) *Anesthesiol* 74:639-642; Hickey et al. (1992) *Anesth. Analg.* 75:602-606; Vaghadia et al. (1999) *Can J. Anaesth.* 46:946-951; each herein incorporated by reference in its entirety). If the block is performed in the morning or early afternoon, patients commonly report postoperative pain during nighttime hours. The need for opioids leads to the potential for opioid-induced side effects, including the inhibition of restorative sleep (Lydic et al., in Sleep and Pain, ed. by G. Lavigne, B J Sessle, M Choinire M, P J Soja, (2007) IASP Press, Seattle, Wash. pp. 99-122; herein incorporated by reference in its entirety) and the potential for airway obstruction and desaturation (Bonafide et al. (2008) *Anesthesiol.* 108:627-633; Bowdle (2004) *Anesth. Analg.* 99:70-76; Rosenberg et al. (1995) *Eur. J. Anaesthesiol. Suppl.* 10:28-30). Ideally, single shot peripheral nerve blocks would provide analgesia throughout the first postoperative night.

Many additives to local anesthetics have been investigated in an attempt to increase the duration of the block in order to improve postoperative pain. The efficacy of clonidine, an $\alpha_2$-adrenoceptor agonist, has been established in a variety of regional anesthesia techniques (Eisenach et al. (1996) *Anesthesiol.* 85:655-674; herein incorporated by reference in its entirety). Clonidine has been shown in clinical studies to prolong the duration of anesthesia and analgesia in peripheral nerve blocks, although results with long acting local anesthetics have been unsuitable (Cucchiaro et al. (2007) *Anesth. Analg.* 104:532-537; Casati et al. (2000) *Anesth. Analg.* 91:388-92; El Saied et al. (2000) *Can. J. Anaesth.* 47:962-967; Eledjam et al. (1991) *Can. J. Anaesth.* 38:870-875; Hutschala et al. (2004) *Eur. J. Anaesthesiol.* 21:198-204; Iohom et al. (2005) *Anesth. Analg.* 100:1179-1183; Iskandar et al. (2003) *Anesth. Analg.* 96:260-262; Iskandar et al. (2001) *Anesth. Analg.* 93:771-775; Reinhart et al. (1996) *Anesth. Analg.* 83:760-765; Singelyn et al. (1992) *Reg. Anesth.* 17:148-150; Singelyn et al. (1996) 83:1046-1050; each herein incorporated by reference in its entirety). Some studies have found no beneficial effect with the addition of clonidine (Culebras et al. (2001) *Anesth. Analg.* 92:199-204; Gaumann et al. (1992) *Anesth. Analg.* 75:69-74; Erlacher et al. (2000) *Acta Anaesthesiol. Scand.* 44:53-57; each herein incorporated by reference in its entirety).

Dexmedetomidine (trade name Precedex®, Hospira, Inc., Lake Forest, Ill.) is a selective $\alpha_2$-adrenoceptor agonist with US Food and Drug Administration approval for continuous intravenous sedation in the intensive care setting and procedural sedation in non-intubated patients. High-dose dexmedetomidine enhanced the duration of sensory and motor blockade when added to bupivacaine in a sciatic nerve block model in rat (Brummett et al. (2008) *Anesthesiol.* 109:502-511; herein incorporated by reference in its entirety). The doses of dexmedetomidine used were between 28-40 µg/kg and did not induce neurotoxicity alone or when mixed with 0.5% bupivacaine. These high doses, however, far exceed that which would be considered safe in humans.

Ropivacaine is now preferred (trade name Naropin®, APP Pharmaceuticals, LLC, Schaumburg, Ill.) in lieu of bupivacaine for peripheral nerve blocks. This preference is based on evidence that local anesthetic-induced cardiac arrest with ropivacaine is more likely to respond to resuscitation efforts than with bupivacaine (Chazalon et al. (2003) *Anesthesiol.* 99:1449-1451; Khoo et al. (2006) *Anaesth. Intensive Care* 34:804-807; Klein et al. (2003) *Anesth. Analg.* 97:901-903; Poley et al. (2003) *Anesth. Analg.* 96:1251-1253; Polley et al. (2003) *Anesthesiol.* 99:1253-1254; each herein incorporated by reference in its entirety).

In experiments conducted during the course of development of certain embodiments of the present invention it was found that dexmedetomidine added to ropivacaine, when compared with ropivacaine alone, enhances the duration of sensory blockade to a heat stimulus in a dose-dependent fashion. Additional analysis determined that the highest doses of perineural dexmedetomidine provide mild, short-term systemic analgesia as measured by sensory response to a heat stimulus to an unblocked control paw. The analgesic effect, however, is localized to the perineural administration and not a central (brain and spinal cord) effect. Low to moderate doses of dexmedetomidine did not have any appreciable systemic effects (delayed emergence from anesthesia (return of righting reflex) or analgesia in the unblocked paw).

The anti-inflammatory effects of perineural clonidine have previously been described in nerve injury models (Lavand'homme et al. (2003) *Pain* 105:247-54; Lavand'homme et al. (2002) *Anesthesiol.* 97(4):972-80; Liu et al. (2006) *Neuroreport.* 17(12):1313-7; Romero-Sandoval et al. (2006) *Anesthesiol.* 104:351-355; Romero-Sandoval et al. (2007) *Brain Behav. Immun.* 21:569-580; Romero-Sandoval et al. (2005) *J. Neurosci.* 25:8988-8994; each herein incorporated by reference in its entirety). Nerve injuries are known to occur during peripheral nerve blocks, and the true incidence is likely underreported (Auroy et al (2002) *Anesthesiol.* 97:1274-80; Brull et al. (2007) *Anesth. Analg.* 104:965-74; Candido et al. (2005) *Anesth. Analg.* 100:1489-95; Gentili et al. (1980) *Can. J Neurol. Sci.* 7:143-51. Hadzic et al. (2004) *Reg. Anesth. Pain Med.* 29:417-23; Hebl (2008) *Anesthesiol.* 108:186-8; Kapur et al. (2007) *Acta Anaesthesiol. Scand.* 51:101-7; Pere et al. (1993) *Reg. Anesth.* 18:304-7; Siegel et al. (2007) *Anesth. Analg.* 105:1820-9; Voelckel et al. (2005) *Anesth. Analg.* 101:1844-6; each herein incorporated by reference in its entirety). Direct trauma to a nerve will cause a natural inflammatory response to the area that is thought to worsen the nerve injury. Local anesthetics are known to cause inflammation, which can worsen nerve and muscle damage. While the present invention is not limited to any particular mechanism, and an understanding of the mechanism is not necessary to practice the present invention, it is contemplated that the addition of dexmedetomidine alone or to local anesthetics decreases perineural inflammation, which attenuated the inflammation and damage that could occur after nerve injury. While the present invention is not limited to any particular mechanism, and an understanding of the mechanism is not necessary to practice the present invention, it is contemplated that by decreasing perineural or muscle inflammation, dexmedetomidine alone or in combination with local anesthetics finds use in lessening or preventing nerve and muscle damage.

Compositions & Kits

Compositions for use in methods of the present invention include, but are not limited to, combinations of anesthetic and/or analgesic agents. Particularly preferred compositions provide analgesia for 9-14 hours or longer (e.g., 15 or more hours, 16 or more hours, 17 or more hours, etc.) with lack of adverse side effects. In certain embodiments, a composition is provided comprising the combination of dexmedetomidine and ropivacine.

Any of the compositions of the present invention, alone or in combination with other compositions of the present invention, may be provided in the form of a kit. The kit may include any and all components necessary or sufficient for administration of peripheral nerve block including, but not limited to, the compositions themselves, syringes, stimulating needles, antiseptic wipes or solutions, sedative agent(s), labels, written and/or pictorial instructions and product information, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

Pharmaceutical Compositions and Routes of Administration

A therapeutic nucleic acid molecule of the present invention can be adapted for use to treat any disease, infection or condition associated with pain, and other indications for which antinociception is desired, alone or in combination with other therapies.

Thus, embodiments of the present invention feature a pharmaceutical composition comprising one or more analgesic and/or anesthetic agent(s) of the invention in an acceptable carrier, such as a stabilizer, buffer, and the like. The compositions of the invention can be administered and introduced into a subject by any standard means, with or without stabilizers, buffers, and the like, to form a pharmaceutical composition. The compositions of the present invention can also be formulated and used as sterile solutions, suspensions for injectable administration, suspensions for continuous infusion, and the other compositions known in the art.

A pharmacological composition or formulation refers to a composition or formulation in a form suitable for administration, e.g., perineural administration, into a subject or proximal to at least one nerve of a subject, including for example wherein the subject is a human. Suitable forms, in part, depend upon the use or the route of entry. Examples of routes of entry include but are not limited to injection (including but not limited to subcutaneous injection), single injection, serial injection, indwelling catheter, continuous infusion, transdermal administration, or transmucosal administration. Such routes of entry should not prevent the composition or formulation from reaching a target cell (i.e., a neuron). For example, injectable pharmacological compositions should be soluble. Other factors are known in the art, and include considerations such as toxicity and forms that prevent the composition or formulation from exerting its effect.

Embodiments of the present invention also include compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference in its entirety. For example, preservatives and stabilizers can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms), e.g. pain. One skilled in the art appreciates that compositions and methods of the present invention find use in multiple types of pain, and that the effective dose may be different for different types of pain. Types of pain include but are not limited to thermal pain, chemical pain, inflammatory pain, ischemic pain, trauamatic pain, blunt pain, sharp pain, prickling pain, and visceral pain. The pharmaceutically effective dose depends on the type of condition (e.g., pain), the composition used, the route of administration, the type of mammal being treated, the physical characteristics of the specific mammal under consideration (including but not limited to age, physical condition, surgical or other medical procedures being performed, circulatory capacity, cardiovascular function, pain tolerance, nerve function, liver function), concurrent medication, and other factors that those skilled in the medical arts will recognize.

Compositions of the present invention can also be administered to a subject in combination with other therapeutic compounds to increase the overall therapeutic effect. The use of multiple compounds to treat an indication can increase the beneficial effects while reducing the presence of side effects.

EXPERIMENTAL

The following examples are provided in order to demonstrate and further illustrate certain preferred embodiments and aspects of the present invention and are not to be construed as limiting the scope thereof.

Example 1

Methods described in Example 1 were employed in the course of experiments described in Example 2, and in Example 3 with modifications as indicated therein.

This study adhered to American Physiological Society and National Institutes of Health guidelines and was approved by the University of Michigan Committee for the Use and Care of Animals (Ann Arbor, Mich.). All procedures were conducted in accordance with the Guide for the Care and Use of Laboratory Animals and the Guidelines for the Care and Use of Mammals in Neuroscience and Behavioral Research.

Drug Preparation

Commercially available 0.75% ropivacaine solution was mixed with preservative free normal saline or dexmedetomidine to make final solutions. The control group received 0.5% ropivacaine alone. In the experimental groups, ropivacaine was mixed with dexmedetomidine to make solutions based on the individual rat's weight 24 hours prior to experimental testing. All experimental groups had a final ropivacaine concentration of 0.5% plus 0.5 μg/kg, 2 μg/kg, 6 μg/kg, or 20.0 μg/kg dexmedetomidine (Table 1). The pH of ropivacaine (5.69±0.05) was used as the standard to which all solutions were maintained.

TABLE 1

The five different study groups are noted below. Groups 2-5 represent the experimental doses that evaluate the dose-dependent effects of dexmedetomidine, in combination with ropivacaine, on the duration of analgesia from a sciatic nerve block. The ropivacaine concentration (0.5%) and total volume injected (0.2 ml) were constant between all groups. Group I represents the control group.

| Group Name | Drug Dose |
| --- | --- |
| Group 1 (n = 10) | Ropivacaine |
| Group 2 (n = 10) | Ropivacaine + 0.5 mcg/kg DEX |
| Group 3 (n = 10) | Ropivacaine + 2.0 mcg/kg DEX |
| Group 4 (n = 10) | Ropivacaine + 6.0 mcg/kg DEX |
| Group 5 (n = 10) | Ropivacaine + 20.0 mcg/kg DEX |

Animal Care and Handling

Fifty male Sprague Dawley rats (caesarean-derived Sprague-Dawley) weighing 250-350 g were purchased from Charles River Laboratories (Wilmington, Mass.). Rats without any signs of neurobehavioral impairment were maintained for one week in 12:12 light-dark cycles with lights on from 6 a.m. to 6 p.m. For the three days prior to surgery and neurobehavioral monitoring, rats were conditioned to the paw withdrawal chambers for one hour per day. Each rat was placed in the same position of the six-chamber container during the conditioning and neurobehavioral testing. On each of the three days prior to testing, both paws of the rat were exposed to the heat stimulus as a portion of the conditioning process. The day before surgery and testing, five PWL baseline measurements were obtained on both the operative and control paws. The mean value of the five measures was recorded as the rat's baseline value.

Paw Withdrawal Latency Testing

The IITC Life Sciences Inc. Plantar Analgesia Meter (Series 8 Model 336T, IITC Life Science Inc., Woodland Hills, Calif.) was used to test paw withdrawal latency (PWL) (Hargreaves et al. (1988) *Pain* 32:77-88; herein incorporated by reference in its entirety). The analgesia meter used a test unit containing a heat source that radiated a light beam. An angled mirror on the test unit was used to locate the correct target on the paw. The meter was set with an active intensity of 40%, an idle intensity of 10%, and a cut-off time for the heat source of 15 seconds. The time to paw withdrawal from the heat stimulus comprised the PWL measure (reaction time was measured to 0.01 s). An acrylic six-chamber container was used to separate the rats that were placed on the glass (Model 400) heated base. In order to decrease the level of variance in PWL measurements, the temperature of the base was set to 30 degrees Celsius five minutes prior to and throughout each round of PWL testing (Ding et al. (1997) *Neurosci. Methods* 76:183-191; herein incorporated by reference in its entirety).

Subfascial Sciatic Nerve Injection

An investigator blinded to the drug condition carried out the sciatic nerve injections. Each rat was randomly assigned to one of the five drug conditions. The laboratory assistants responsible for drug preparation were blinded to the surgery, neurobehavioral monitoring, and PWL measures. Rats were anesthetized and maintained with 2.5% isoflurane. The sciatic nerve of the left hind extremity was exposed using a lateral incision over the thigh and division of the superficial fascia as previously described (Brummett et al. (2008) *Anesthesiol.* 109:502-51; Gerner et al. (2005) *Reg. Anesth. Pain Med.* 30:344-350; Hung et al. (2005) *Anesthsiol.* 103:1246-1252; Kau et al. (2006) *Reg. Anesth. Pain Med.* 31:14-18; each herein incorporated by reference in its entirety). Following the dissection, the sciatic nerve was clearly identified at a point proximal its bifurcation. All rats received unilateral injections of 0.2 ml of drug into the perineural space below the clear fascia covering the nerve and proximal to the bifurcation of the sciatic nerve. Injections were made using a tuberculin syringe and a 30-gauge needle. The time of the injection was recorded and deemed the zero time point. A non-absorbable muscle fascia suture was placed at the midpoint of the injection site as a marker for subsequent nerve removal. The suture was placed in the muscle fascia of the biceps femoris below the subcutaneous tissue and was neither directly touching nor surrounding the nerve (Brummett et al. (2008) *Anesthesiol.* 109:502-51; herein incorporated by reference in its entirety). The incisions were closed and isoflurane was discontinued.

Neurobehavioral Examination and PWL Testing

Following the sciatic nerve injection, the incision was closed and the anesthetized rat was returned to its cage and placed supine. The time to the return to a prone position (recovery of righting reflex [RoRR]) was recorded to the nearest minute. After righting, rats were placed in the chamber for PWL testing. Three PWL measures from both the operative and control paw were obtained every 30 min from the time of the injection. The mean value of the three measures at each time point was calculated. Measurements were taken every 30 minutes until three consecutive PWL values at or below the baseline measurement were obtained. All rats were monitored for at least 210 minutes. In addition, the motor function of the surgical hind paw was assessed every 30 minutes by observation as either a curled paw (motor score=1, indicates motor blockade) or normal paw position (motor score=0, no motor blockade) (Brummett et al. (2008) *Anesthesiol.* 109:502-51; Dyhre et al. (2006) *Reg. Anesth. Pain Med.* 31:401-408; Soderberg et al. (2006) *Anesthiol.* 104:110-121; each herein incorporated by reference in its entirety). Once the rat had returned to baseline sensory and motor function, it was returned to its home cage. The next morning, five PWL measurements were obtained prior to nerve removal for future analysis. In rats scheduled for nerve collection at 14 days post-injection, an additional five PWL measurements were taken immediately prior to nerve removal and euthanasia.

Histopathological Evaluation

Following the neurobehavioral examination, rats were assigned to one of two groups for sciatic nerve removal and pathologic evaluation. Nerves were removed under general anesthesia at 24 hours or 14 days. Approximately 1.5 cm of nerve was removed with the injection site at the midpoint as marked by the fascial suture in the muscle directly above. In order to avoid any trauma-induced artifacts, care was taken not to stretch the nerves during the removal process. Nerves were placed in 2.5% glutaraldehyde for 24-72 hours, then washed three times and placed in a phosphate buffer. Seven nerves in the 20 μg/kg dexmedetomidine group (three at 24 hours and four at 14 days) were analyzed. Nerves were cut into 5-micron sections and stained with hemotoxylin and eosin and Luxol fast blue. Those nerves not analyzed were stored at 4° C.

A pathologist, blinded to experimental treatment, analyzed the slides using previously established scales for perineural inflammation (0=no inflammation, 1=small focal areas of mild edema and/or cellular infiltrate, 2=locally extensive areas of moderate edema/cellular infiltrate, 3=diffuse areas of moderate to marked edema/cellular infiltrate) and signs of nerve damage (0=no lesions, 1=0-2% of the fibers with lesions in axons or myelin, 2=2-5% with lesions, 3=>5% with lesions) (Brummett et al. (2008) *Anesthesiol.* 109:502-51; Kytta et al. (1986) *Acta Anaesthesia Scand.* 30:625-629' Pere et al. (1993) *Reg. Anest.* 18:304-307; each herein incorporated by reference in its entirety).

Statistics

Sensory time-course data and RoRR are presented as means±SEM. Motor data are presented as medians and interquartile ranges. Data were analyzed using SAS 9.2 (SAS Institute Inc., Cary, N.C.). A proportional hazards survival analysis (Cox Model) was used to compare the duration of a dense sensory blockade across doses (defined as the time when PWL went below 14 seconds for three consecutive time periods), the time to return to normal (defined as PWL<6.59 sec [baseline PWL plus 1 standard deviation for all 50 rats]), the time to return to normal motor function (time period at which the paw was seen to be normal, motor score=0), and the RoRR (time period in minutes after discontinuation of isoflurane to the rat turning from a supine to prone position) (Allison (1995) in Survival Analysis Using SAS: A Practical Guide, ed. by P D Allison, N D Cary, SAS Publishing, pp 111-134; herein incorporated by reference in its entirety). Posthoc tests were used to compare PWL measures at different drug doses, with a Bonferroni correction for multiple comparisons ($\alpha$=0.005 was used for each of the 10 post-hoc comparisons). A repeated-measures ANOVA evaluated the effects of dose, time, and dose by time on PWL of the operative and control paws. Post-hoc tests were completed for between group comparisons at time points 90-210 minutes using a Bonferroni test for multiple comparisons ($\alpha$=0.005 was used for each of the 10 post-hoc comparisons).

Example 2

Perineural Dexmedetomidine Added to Ropivacine Caused a Dose-Dependent Increase in the Duration of Thermal Antinociception in Sciatic Nerve Block in Rat Dexmedetomidine added to ropivacaine increased the duration of analgesia to a heat stimulus in a dose-dependent fashion (FIG. 1). The duration of dense sensory blockade (defined as PWL≧14 sec) was increased in a dose-dependent fashion when the ropivacaine group was compared with all dexmedetomidine groups (p<0.001). Dense sensory blockade was significantly longer when highest dose dexmedetomidine group (20 μg/kg) was compared with all other dexmedetomidine groups (p<0.005). The time to return to baseline sensory function (defined as PWL<6.59 sec) was significantly longer in the 2.0, 6.0, and 20.0 μg/kg dexmedetomidine groups when compared with ropivacaine alone (p<0.003). Intergroup increases in time to return to normal sensory function were also seen when 20 μg/kg was compared with 0.5 and 2.0 μg/kg dexmedetomidine (p<0.001) and when 6.0 μg/kg was compared with 0.5 μg/kg dexmedetomidine (p<0.0001).

Figure 6:
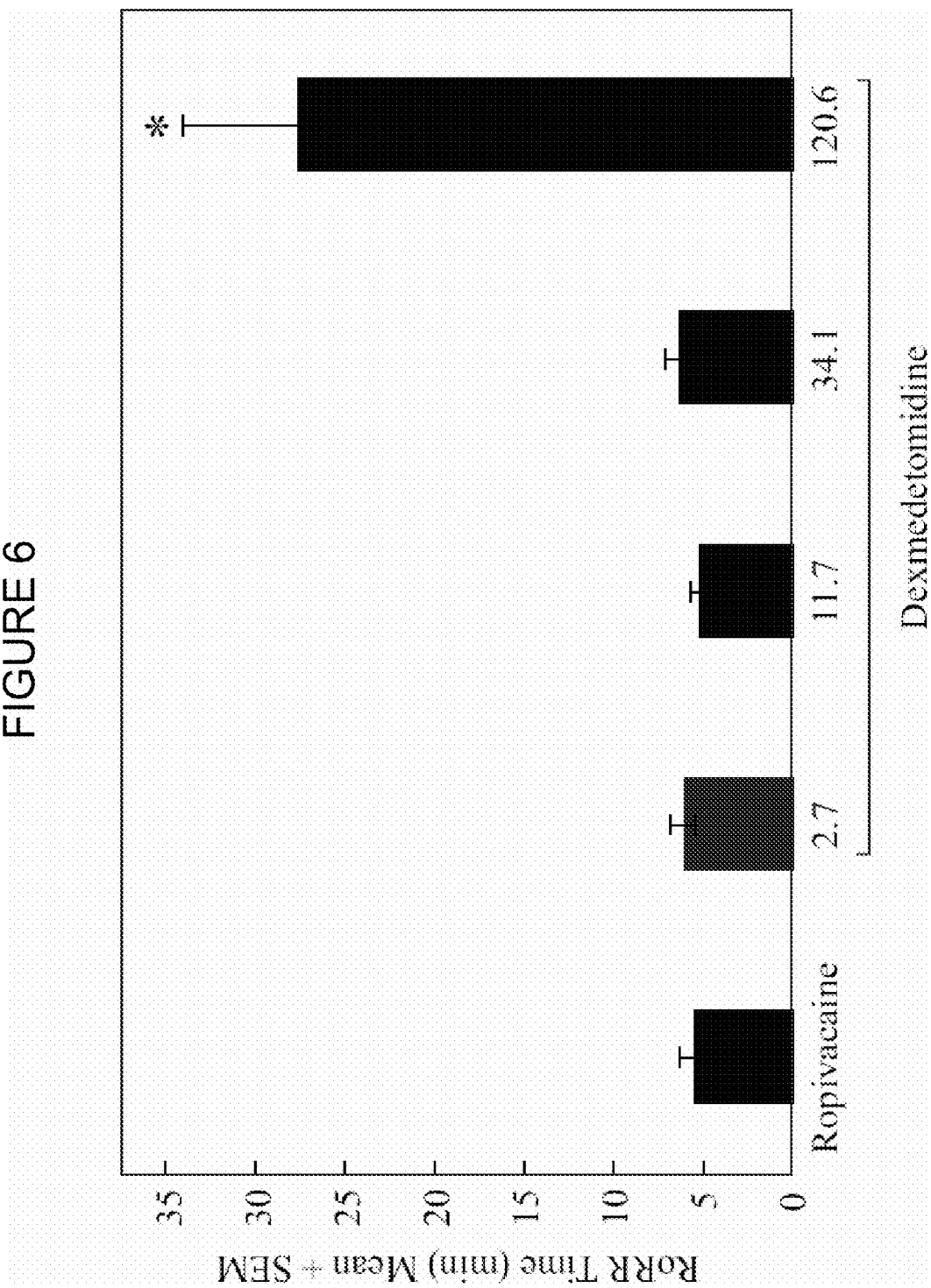
FIG. 6 shows that the highest dose of dexmedetomidine (20 µg/kg) caused sedative effects immediately following anesthesia that prolonged the time to recovery of righting reflex (RoRR) when compared to all other groups ($p<0.005$). There were no other significant differences in RoRR. Total anesthesia time and percent isoflurane were not different between groups.

There was a significant time (p<0.0001), dose (p<0.0001), and time by dose effect (p<0.0001) on the PWL of the operative paws. There were missing PWL measurements at time points 30 and 60 min in some groups due to increased righting times (FIG. 6). Missing PWL measures also occurred after 240 min due to a return to normal sensory function in some rats. Therefore, intergroup analyses by time points were restricted to the 90-210 min interval (Table 2). PWL at time points 120 and 150 min were significantly longer in all dexmedetomidine groups when compared with the ropivacaine group (p<0.001, FIG. 2). At time points 180 and 210 min, PWL measures in the two highest dexmedetomidine groups (6.0 and 20.0 μg/kg) were significantly longer than when ropivacaine was administered alone (p<0.001, FIG. 2). There were also multiple time point differences when comparing between the dexmedetomidine groups (p<0.003, FIG. 3).

TABLE 2

Figure 2:
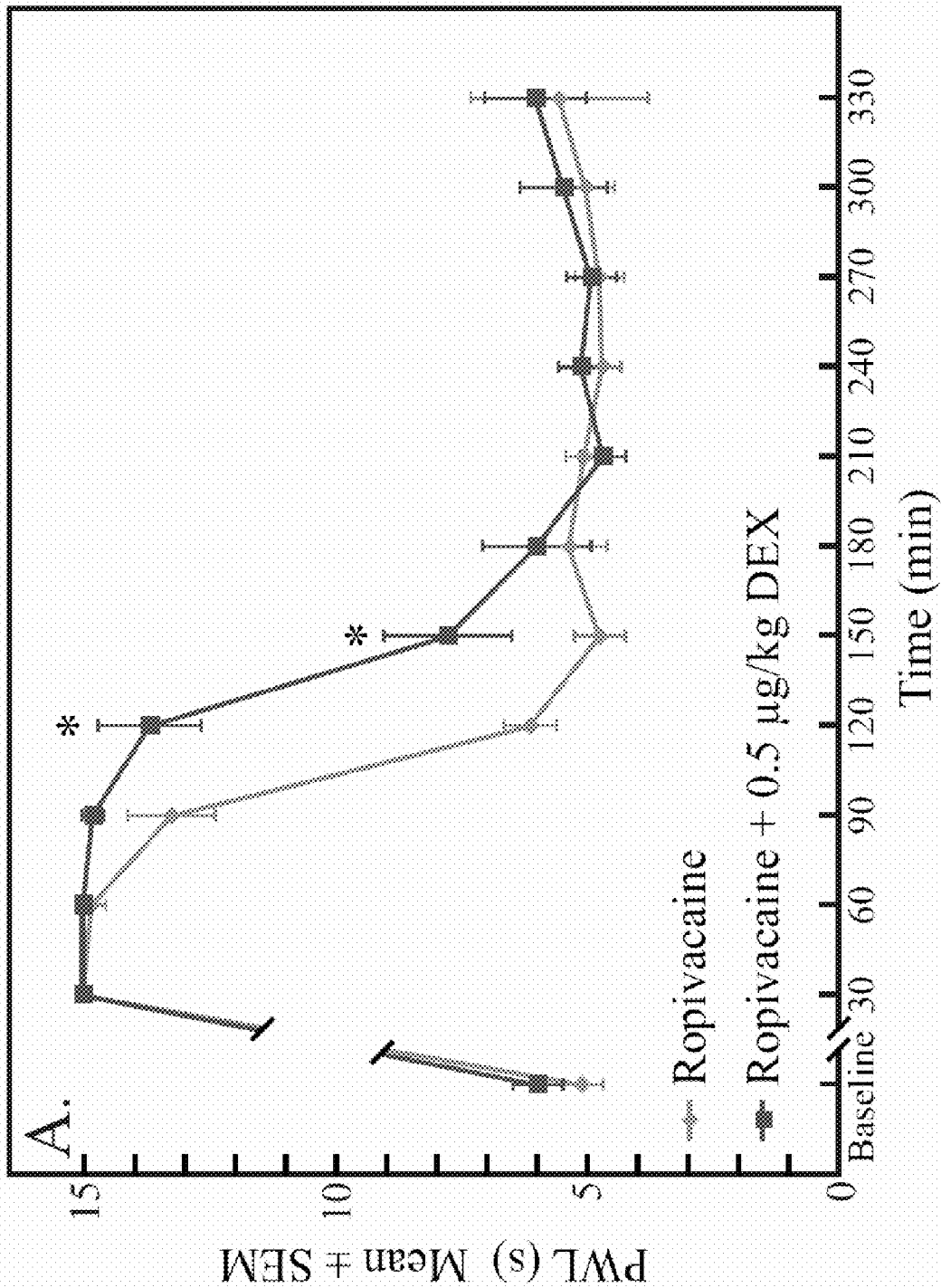
FIG. 2 shows that increasing doses of dexmedetomidine prolonged the duration of paw withdrawal latency to a heat stimulus when compared to the ropivacaine control group. Between group comparisons from 90-210 min found multiple significant differences at individual time points. * indicates statistically significant values, $p<0.005$.
Figure 2:
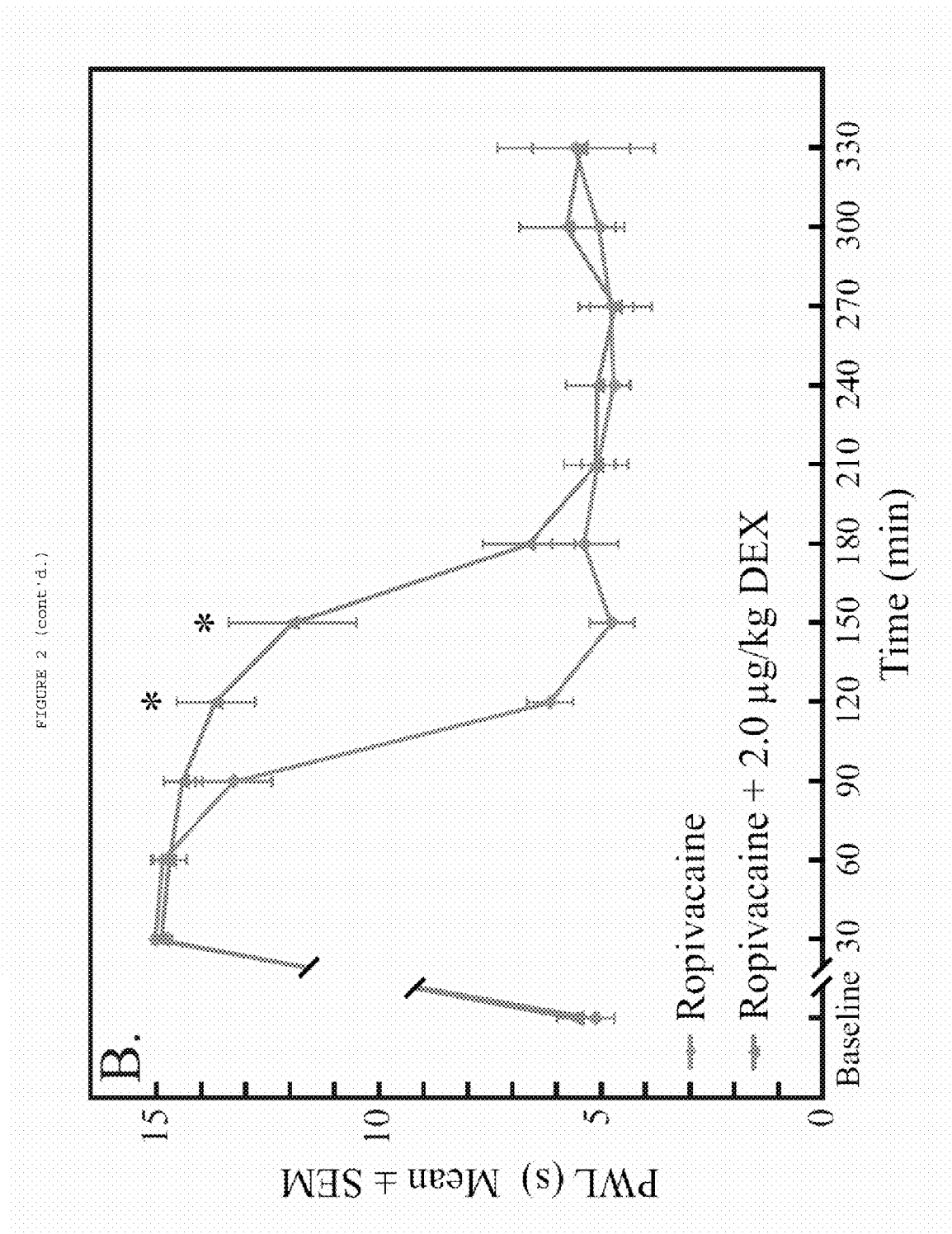
Figure 2:
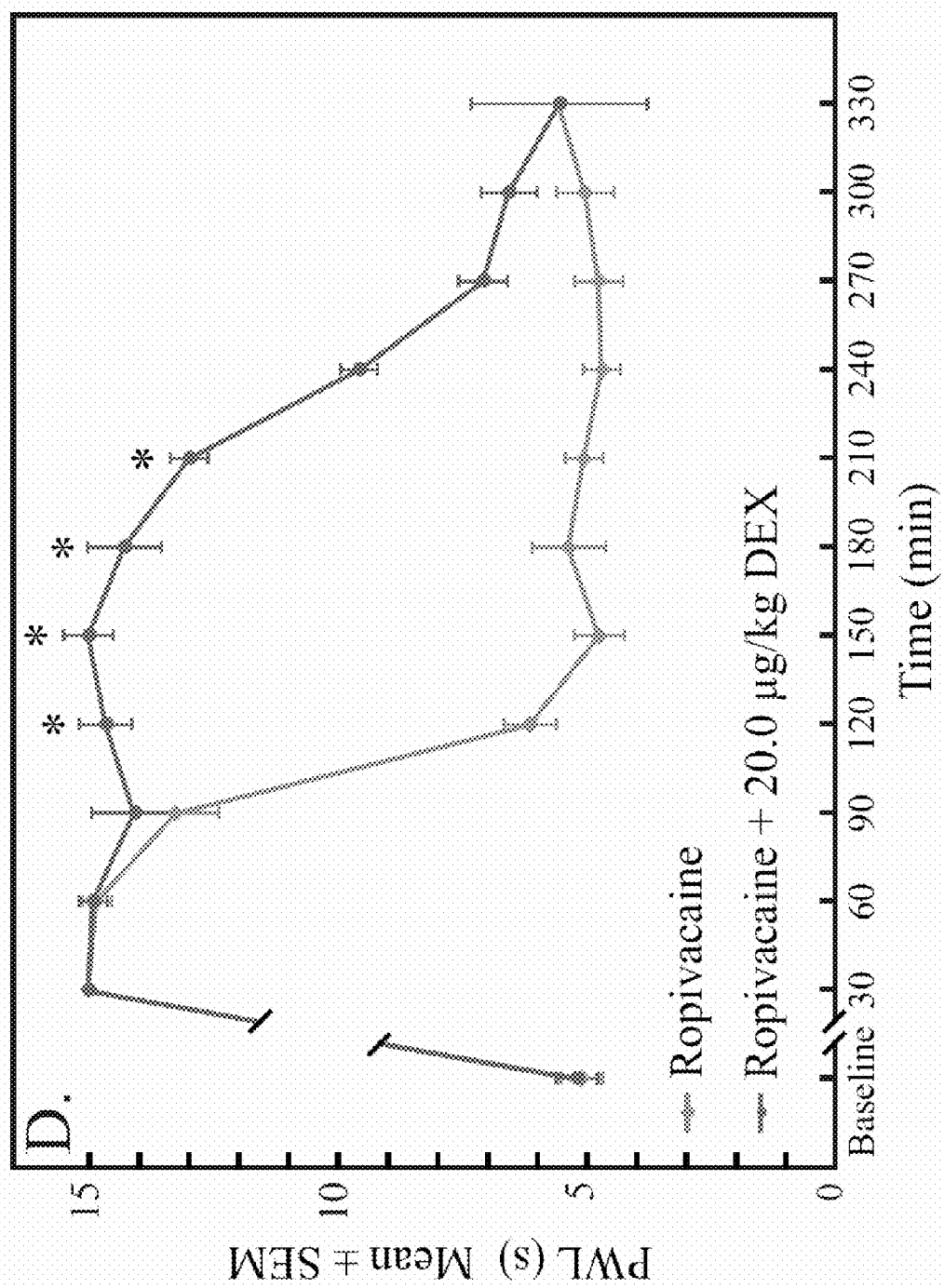
Figure 3:
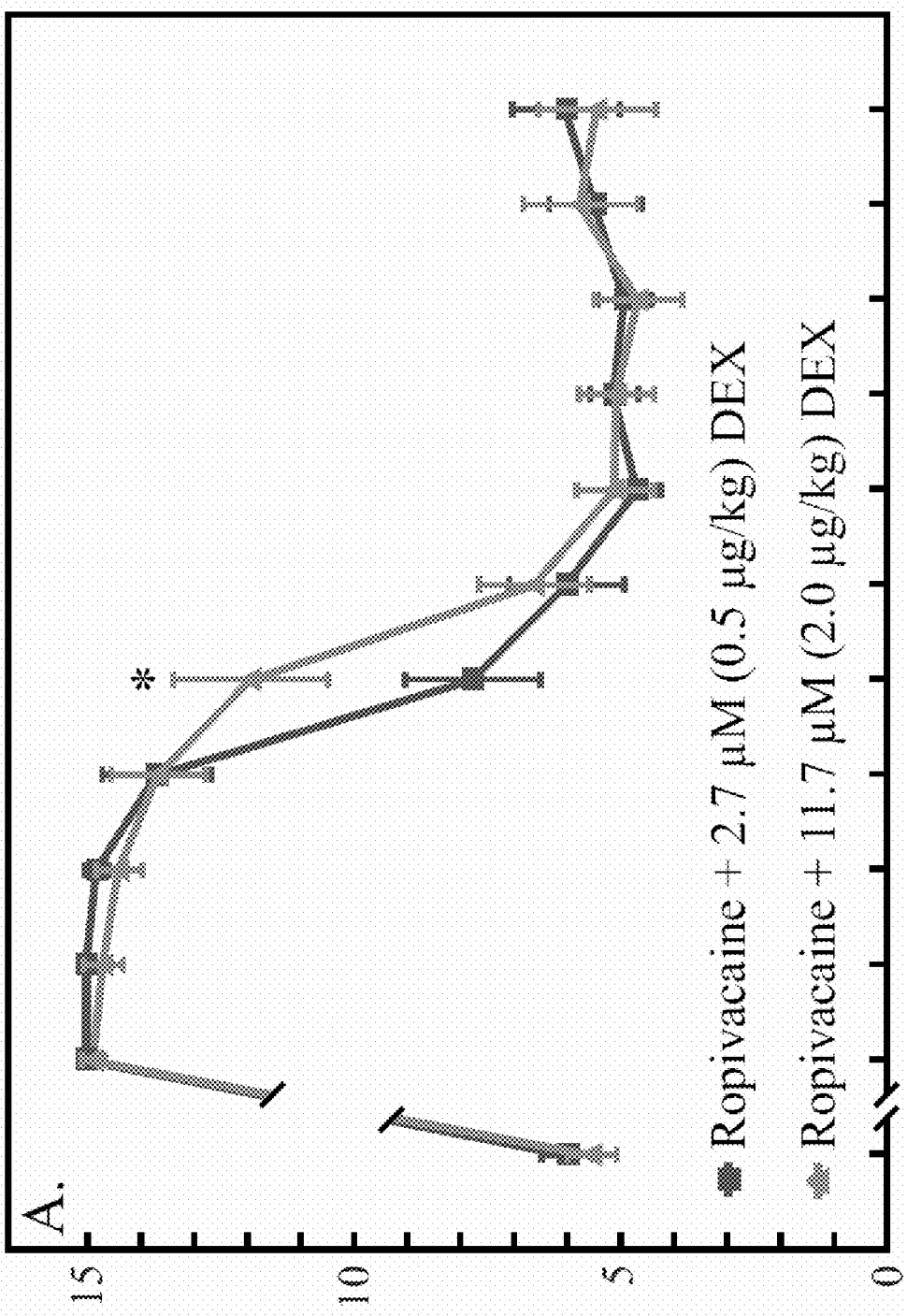
FIG. 3 shows that between group comparisons from 90-210 min for the dexmedetomidine groups also found multiple significant differences at individual time points. * indicates statistically significant values, $p<0.005$.
Figure 3:
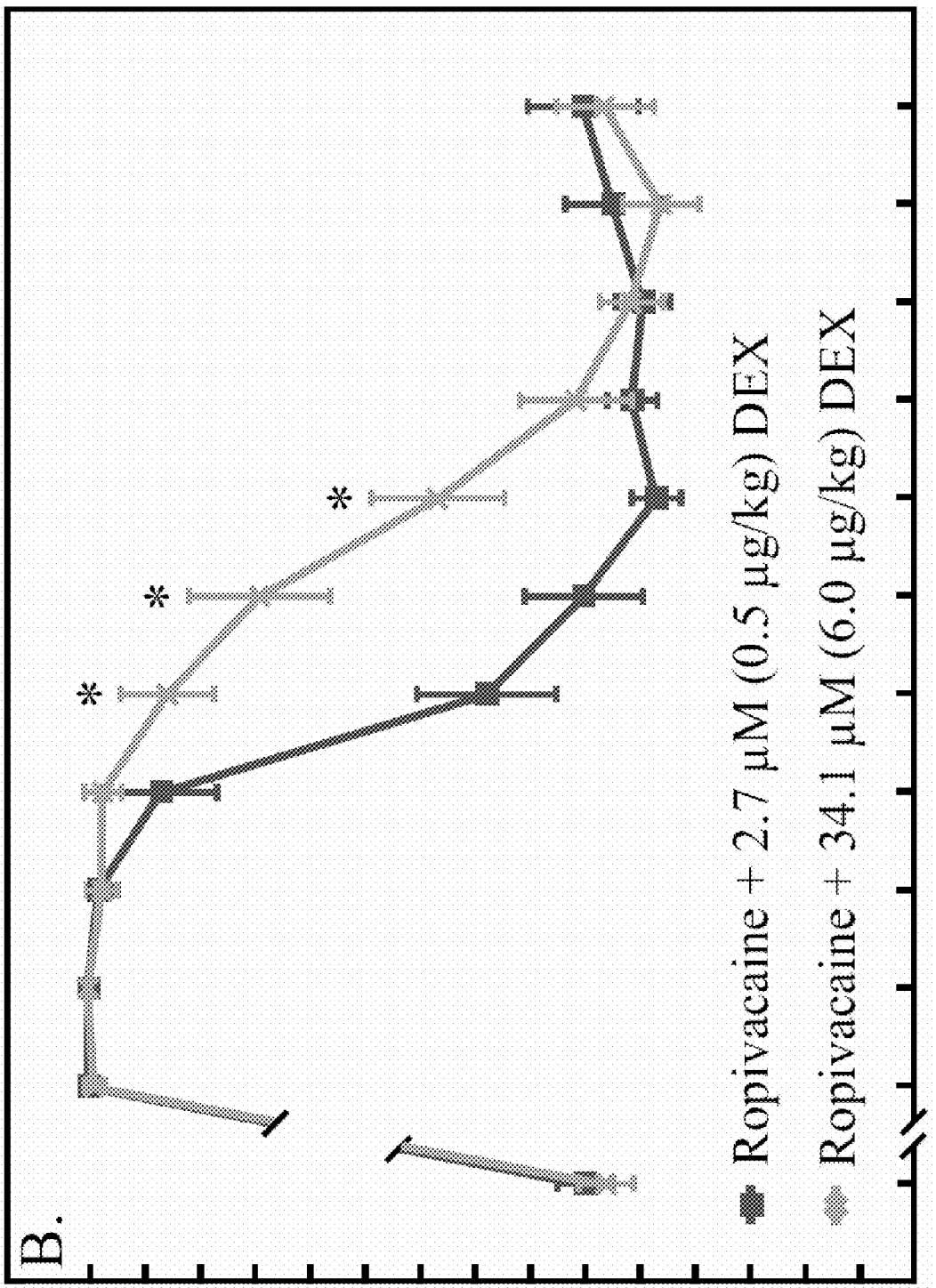
Figure 3:
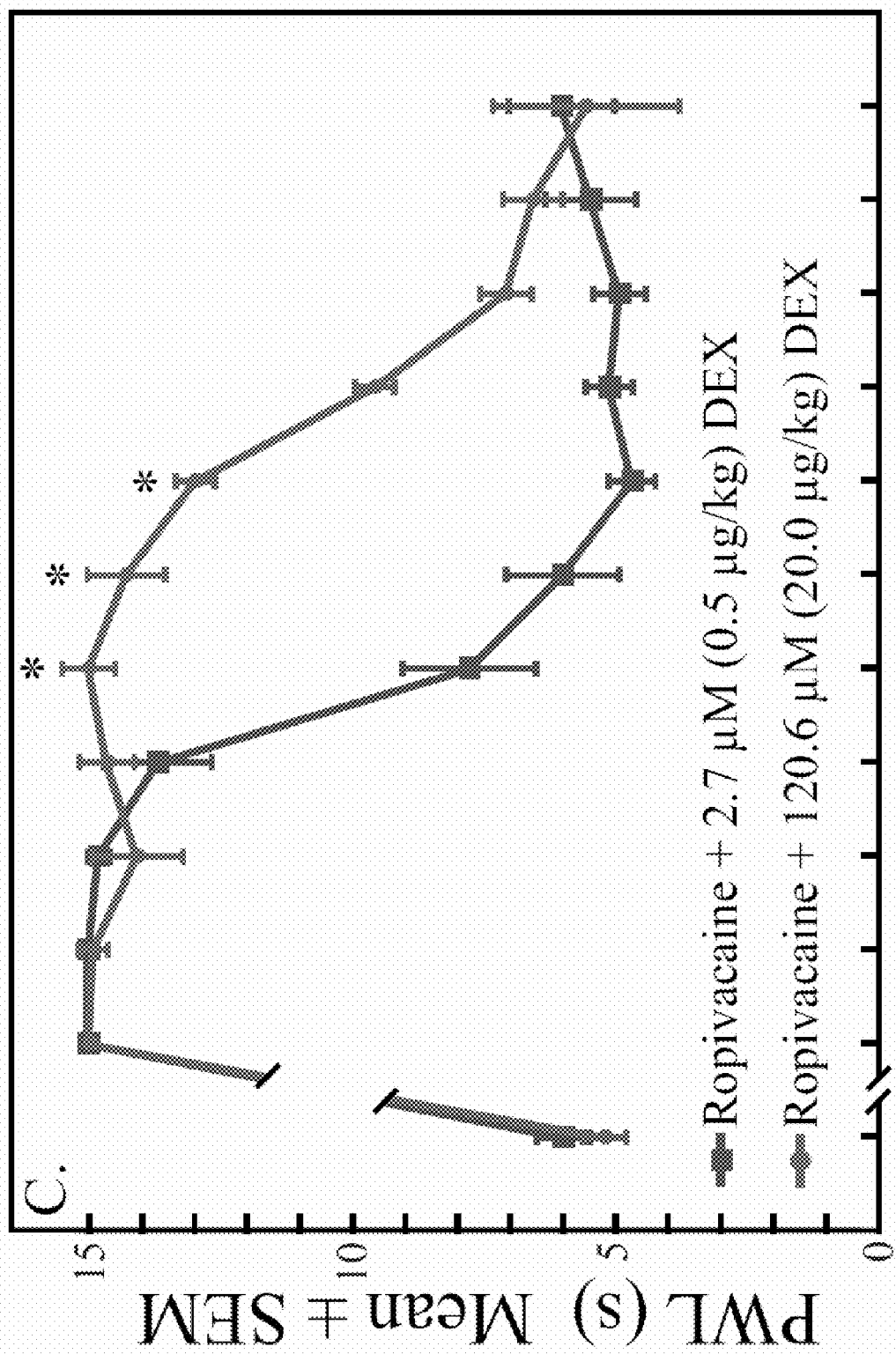
Figure 3:
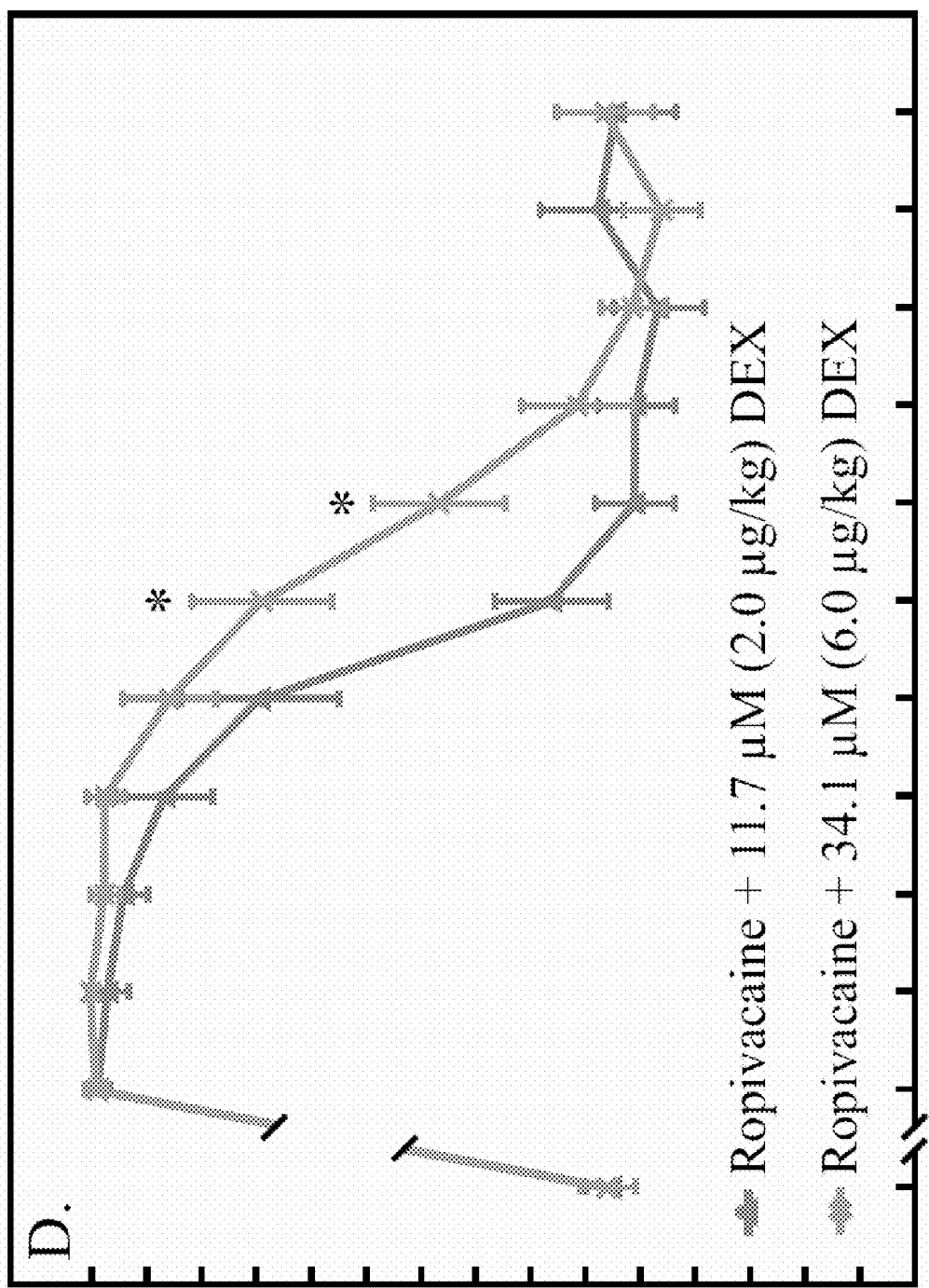
Figure 3:
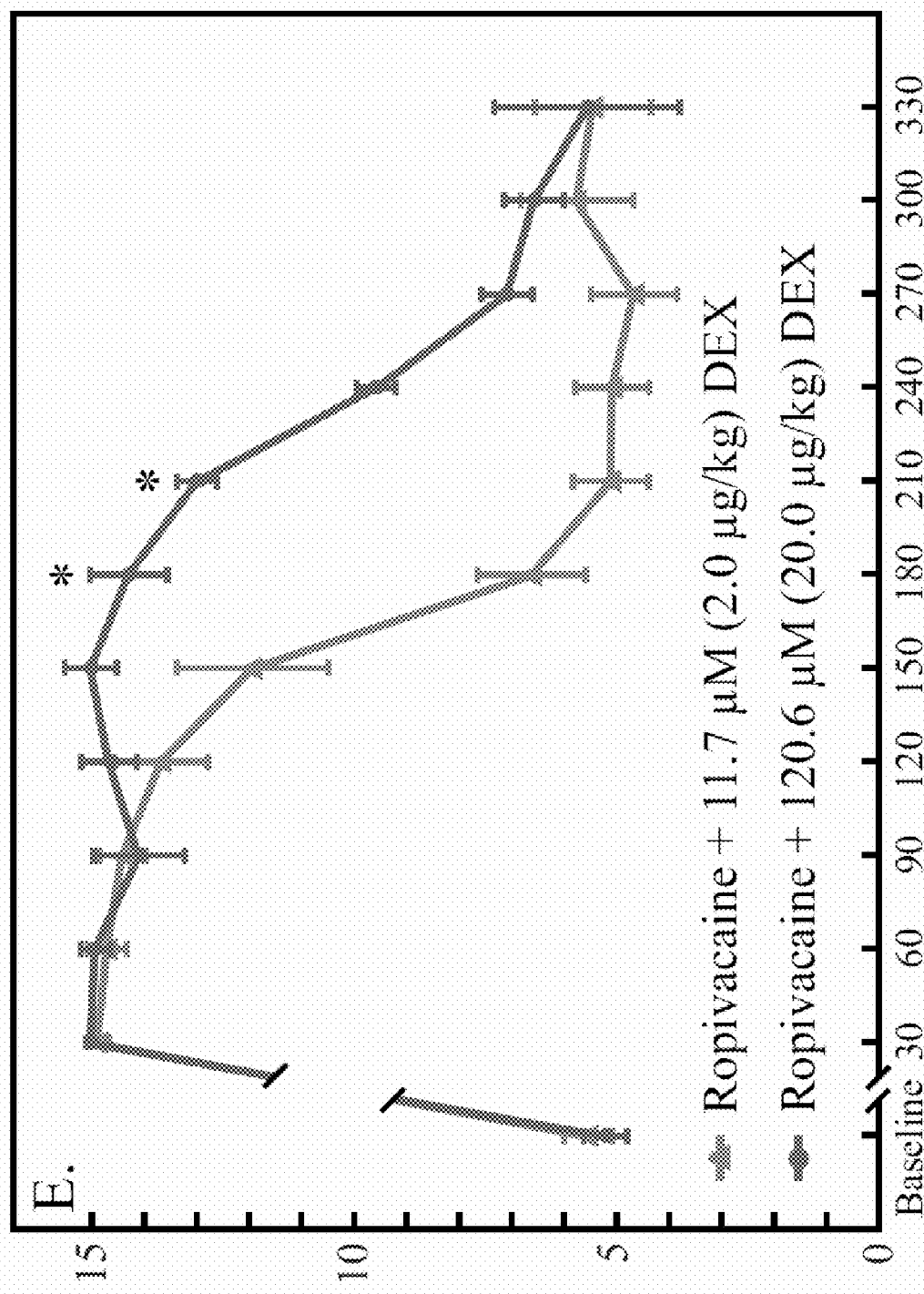
Figure 3:
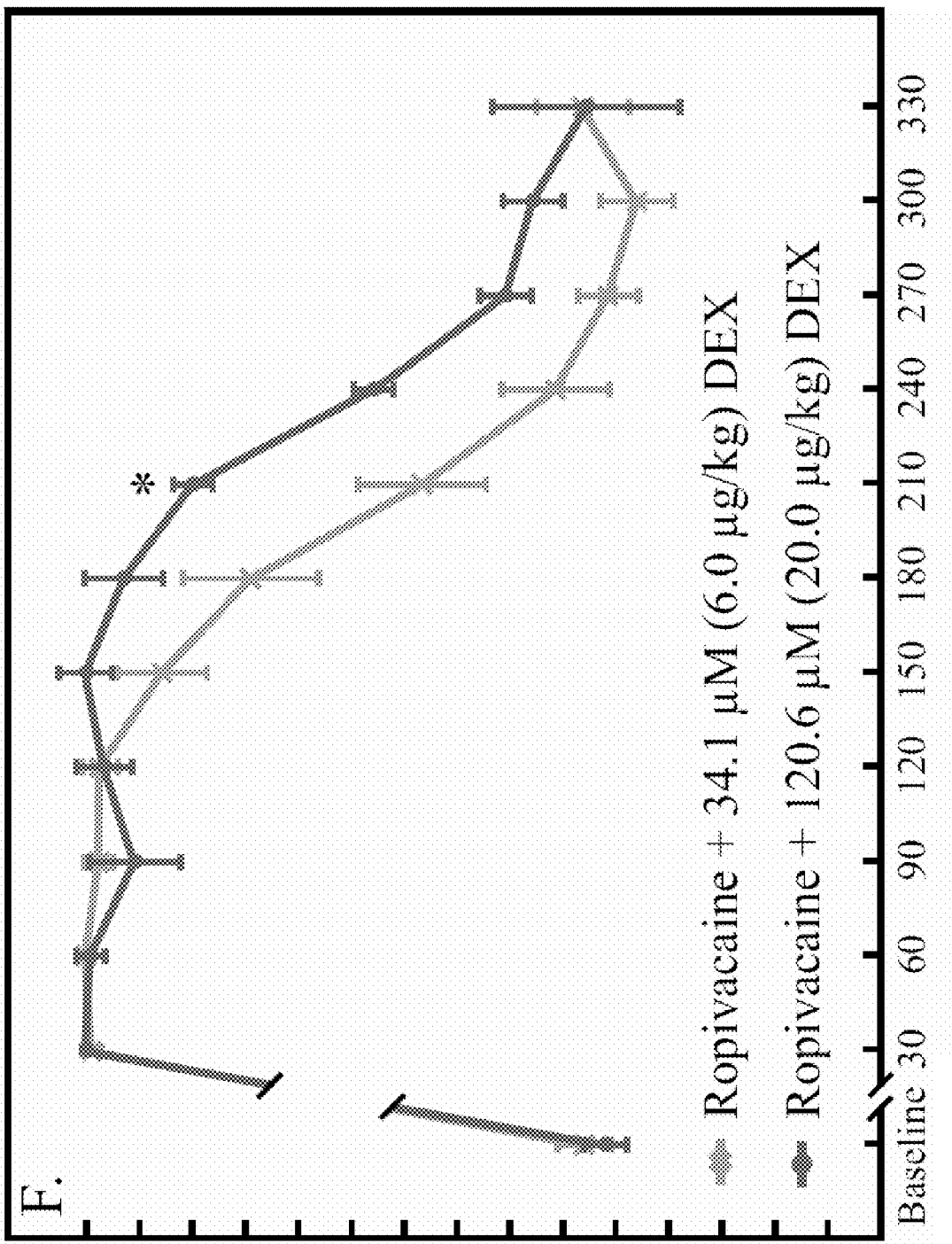

Paw withdrawal latency values at time points 90-210 min. Paw withdrawal latency (PWL) measurements by time point were analyzed from 90-210 min (FIGS. 2 and 3).

|  | 90 min | 120 min | 150 min | 180 min | 210 min |
| --- | --- | --- | --- | --- | --- |
| Ropivacaine Mean PWL values (sec) | 13.25 | 6.13 | 4.74 | 5.35 | 5.05 |
| SEM | 0.87 | 0.53 | 0.50 | 0.74 | 0.38 |
| Ropivacaine + 0.5 μg/kg DEX Mean PWL values (sec) | 14.81 | 13.68 | 7.76 | 5.99 | 4.67 |
| SEM | 0.22 | 1.02 | 1.27 | 1.07 | 0.44 |
| Ropivacaine + 2.0 μg/kg DEX Mean PWL values (sec) | 14.40 | 13.66 | 11.93 | 6.60 | 5.09 |
| SEM | 0.44 | 0.88 | 1.45 | 1.04 | 0.72 |
| Ropivacaine + 6.0 μg/kg DEX Mean PWL values (sec) | 14.75 | 14.74 | 13.56 | 11.89 | 8.65 |
| SEM | 0.27 | 0.34 | 0.85 | 1.28 | 1.21 |
| Ropivacaine + 20.0 μg/kg DEX Mean PWL values (sec) | 14.08 | 14.65 | 15.00 | 14.28 | 12.98 |
| SEM | 0.73 | 0.38 | 0.00 | 0.71 | 1.21 |

DEX = dexmedetomidine,
min = minutes,

TABLE 2-continued

Paw withdrawal latency values at time points 90-210 min. Paw withdrawal latency (PWL) measurements by time point were analyzed from 90-210 min (FIGS. 2 and 3).

| | 90 min | 120 min | 150 min | 180 min | 210 min |
|---|---|---|---|---|---| sec = seconds.

Figure 4:
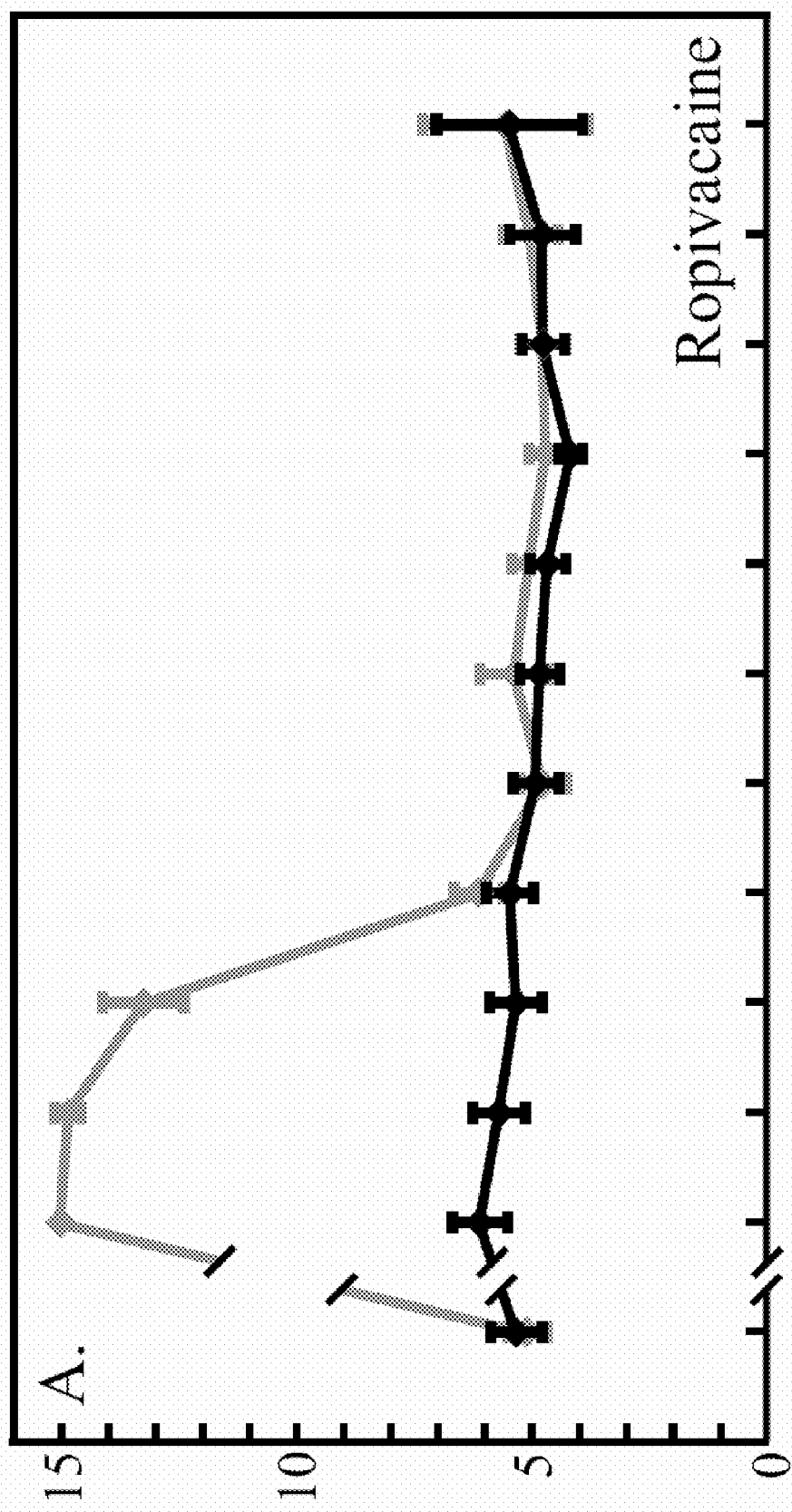
FIG. 4 shows paw withdrawal latency values of the operative paw versus the unblocked control paw for each drug dose. The analgesic effects of ropivacaine (FIG. 4A) and ropivacaine plus different doses of dexmedetomidine (FIG. 4B-E) were significantly greater in the operative paws. There was little systemic analgesic effect of dexmedetomidine as measured by paw withdrawal latencies of the unblocked control paws.
Figure 4:
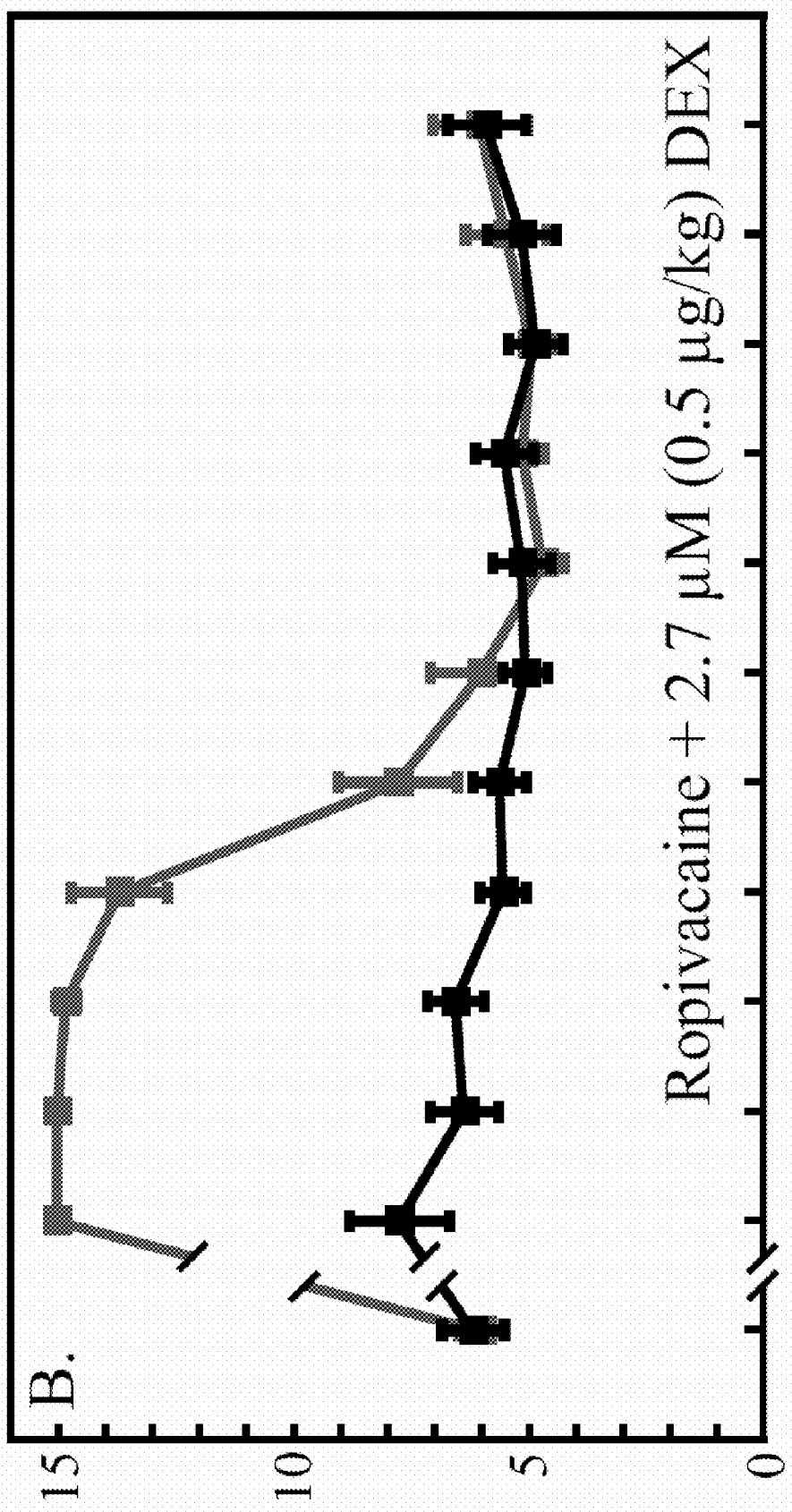
Figure 4:
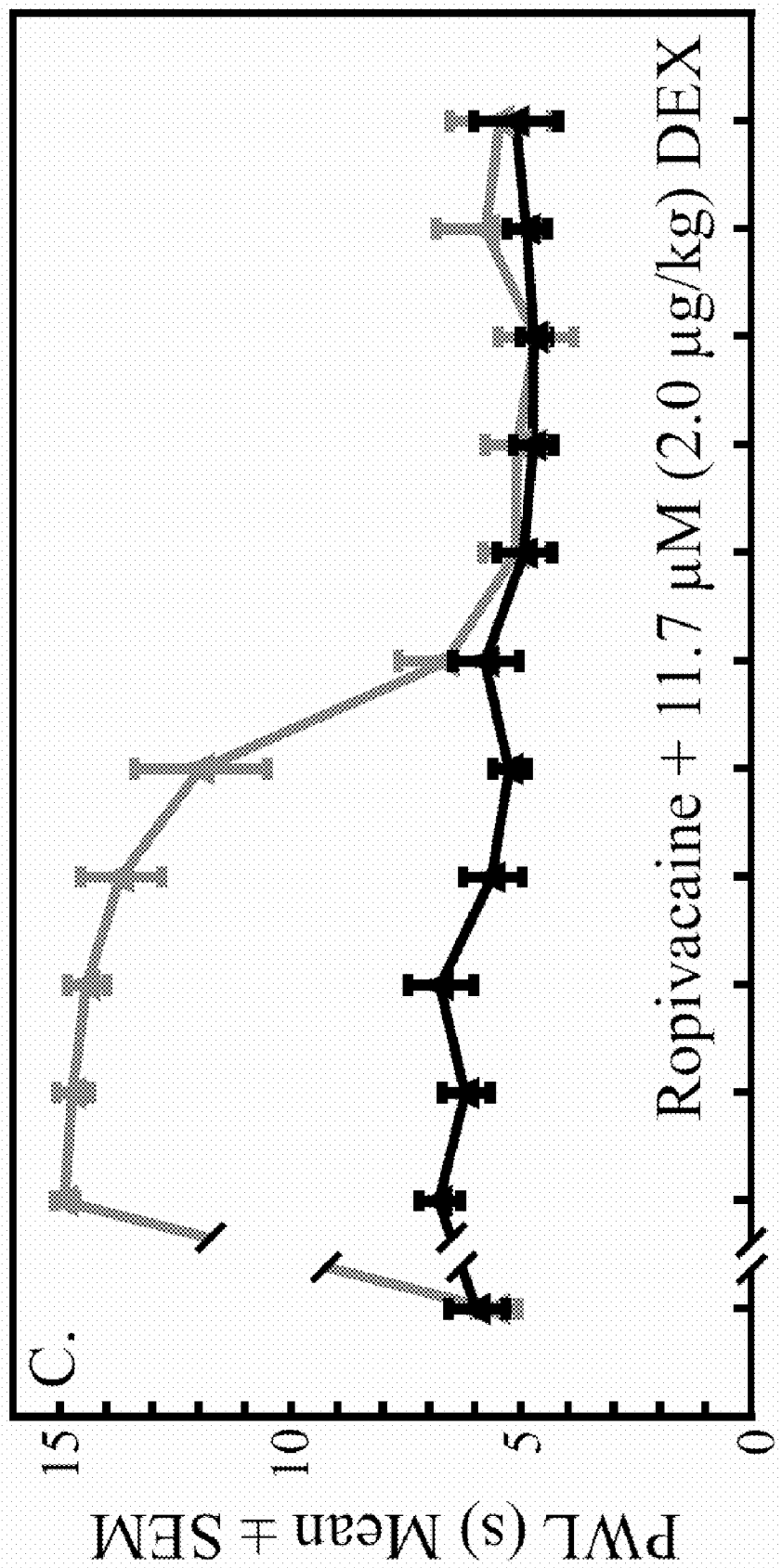
Figure 4:
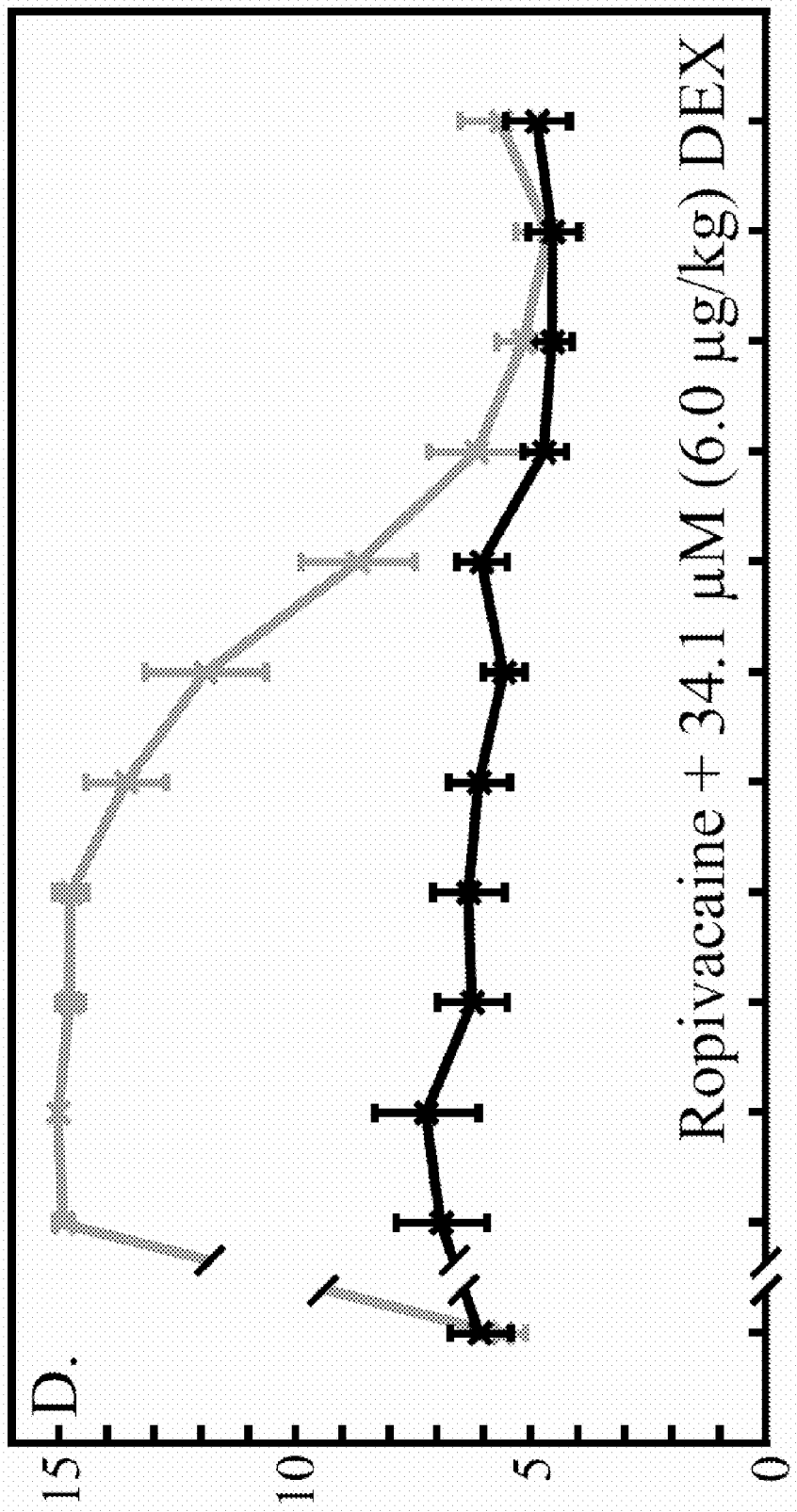
Figure 4:
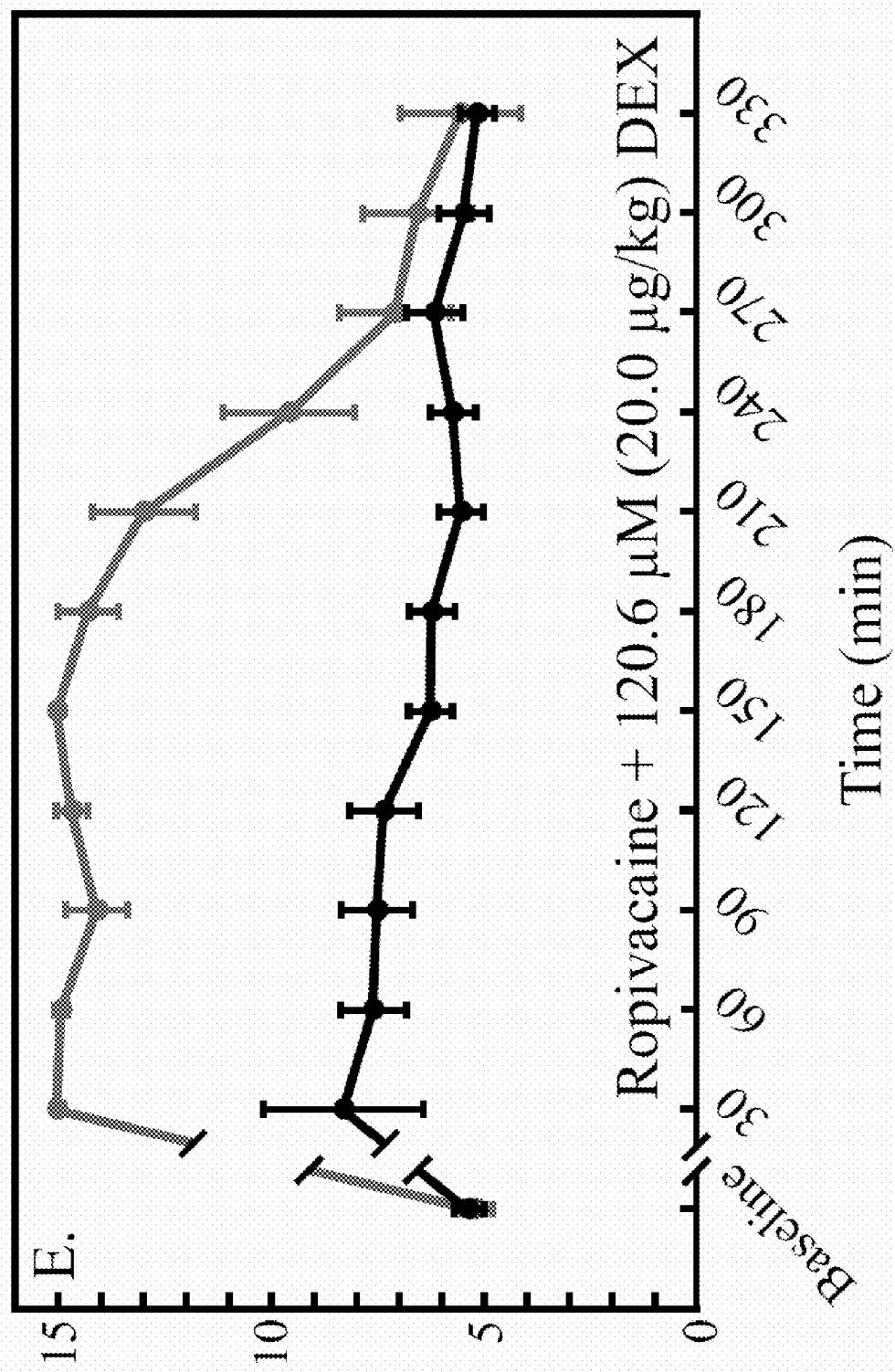

All rats showed significantly longer PWL measurements for the operative paw when compared with the control paw (FIG. 4). PWL for control paws between all groups were also analyzed between 90-210 min. The highest dose dexmedetomidine group (20.0 µg/kg) had significantly longer PWL of the control paw at 90 minutes when compared with the ropivacaine control (p<0.005). Although the mean PWL for the control paws in all of the dexmedetomidine groups were higher than the ropivacaine group, there were no other significant differences in the PWL of the control paws between groups.

Figure 5:
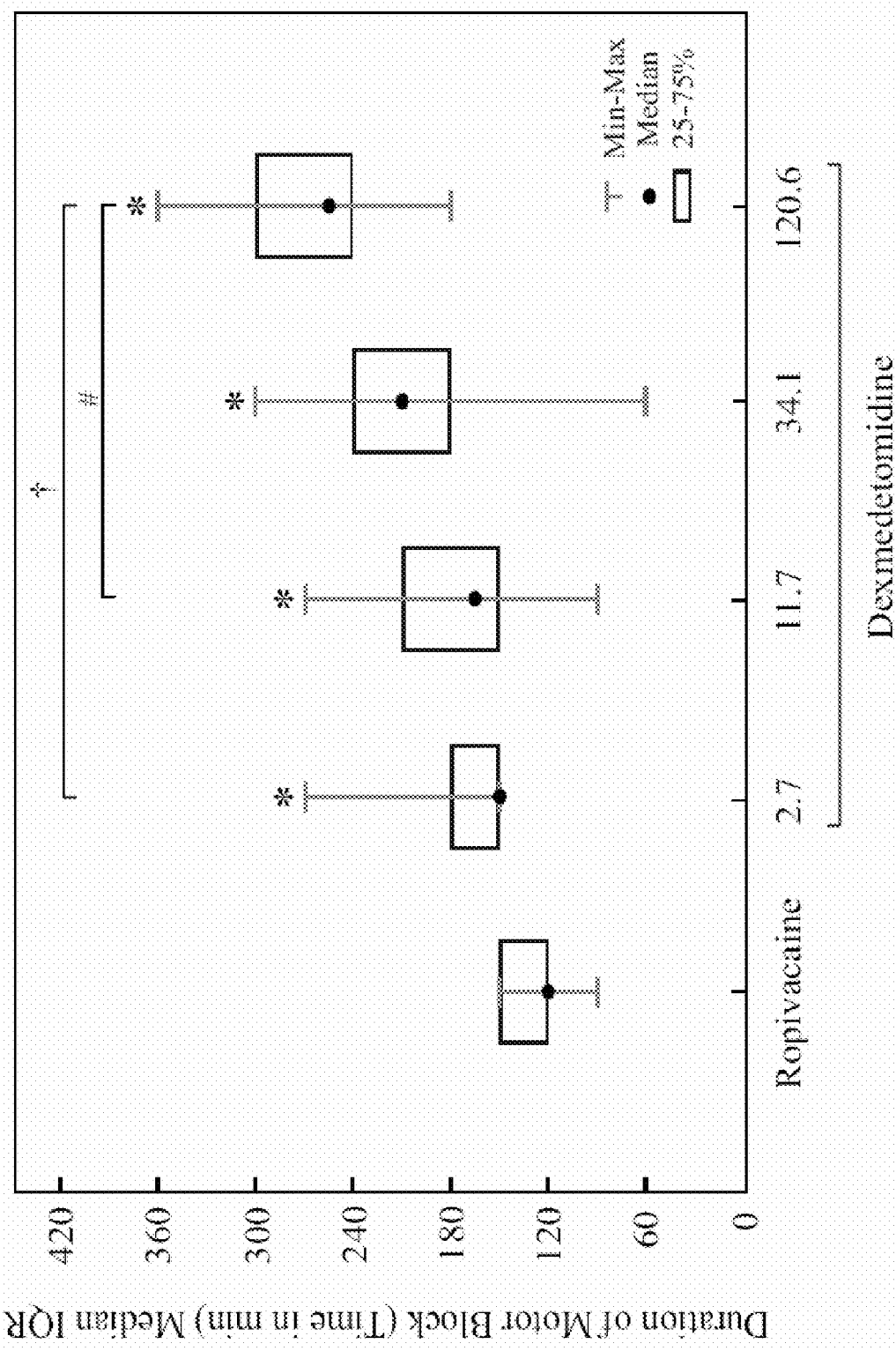
FIG. 5 shows that there was a direct increase in the duration of motor blockade with increasing doses of dexmedetomidine added to ropivacaine for sciatic nerve blockade. A motor block was identified by the observation of a curled paw (motor score=1). A return to normal paw posture was given a motor score of 0. * All doses containing dexmedetomidine were significantly different from ropivacaine administered alone ($p<0.003$). † and # indicate significant differences between the highest dose dexmdetomidine group and the 0.5 and 2.0 µg/kg groups, respectively ($p<0.002$).

Motor blockade was significantly longer in all dexmedetomidine groups compared with ropivacaine alone (p<0.003, FIG. 5). Intergroup increases in time to return to normal motor function was seen when the 20.0 µg/kg dexmedetomidine group was compared with 0.5 and 2.0 µg/kg groups (p<0.002). Otherwise, there were no significant differences in the duration of motor blockade between the different dexmedetomidine groups.

There were no between group differences in the total anesthesia times or isoflurane levels (p=0.24) for anesthesia maintenance (p=0.31). There were no differences in RoRR times between the ropivacaine group and the 0.5, 2.0 and 6.0 µg/kg dexmedetomidine groups. The 20.0 µg/kg dexmedetomidine group had significantly longer RoRR times when compared with all other groups (p<0.002, FIG. 6).

Histopathologic analysis revealed normal axons and myelin in all six of the nerves analyzed in the 20 µg/kg dexmedetomidine group (Pathology score=0, no nerve lesions). The three nerves analyzed at 24 hours showed mild to moderate, locally extensive to diffuse, perineural congestion and lymphocytic/plasmacytic inflammatory cell infiltrates (Inflammation score=1-2). The pathology did not, however, extend to the nerves. There was no significant perineural inflammation in the four nerves analyzed at 14 days (Inflammation score=0).

This is the first study showing that dexmedetomidine added to ropivacaine increases the duration of sensory motor blockade to a thermal stimulus in rat. The time of dense sensory blockade and time to recovery of normal sensory function were increased in a dose-dependent manner with progressively higher doses of dexmedetomidine (FIG. 1). At multiple time points between 90-210 minutes, there were significant differences between the ropivacaine control group and all dexmedetomidine groups (FIG. 2), as well as differences between the different dexmedetomidine doses (FIG. 3).

Clinically relevant doses of dexmedetomidine (0.5, 2.0, and 6.0 µg/kg) enhanced blockade when added to ropivacaine. Previous work showed enhanced sensory and motor blockade when high-dose dexmedetomidine (28-40 µg/kg) was added to bupivacaine in sciatic nerve blocks in rat (Brummett et al. (2008) Anesthesiol. 109:502-51; herein incorporated by reference in its entirety). The US Food and Drug Administration approved dose for intravenous sedation of mechanically ventilated patients in the intensive care unit is a bolus dose of dexmedetomidine (1 µg/kg) over 10 minutes, followed by an infusion of 0.2-0.7 µg/kg/hr. Significantly higher intravenous infusion doses have been described without ill effect (Ramsay et al. (2004) Anesthesiol. 101:787-790; herein incorporated by reference in its entirety). Although it is not possible to predict the potential systemic absorption of dexmedetomidine from the perineural space, the doses used herein approach approved intravenous doses and would not have significant systemic side effects.

Dexmedetomidine provides analgesia and sedation without respiratory depression when given intravenously (Ramsay et al. (2004) Anesthesiol. 101:787-790; Martin et al. (2003) J. Intensive Care med. 18:29-41; Ramsay et al. (2006) J. Clin. Anesth. 18:452-454; Venn et al. (2001) Br. J. Anaesth. 87:684-690; each herein incorporated by reference in its entirety), and the centrally mediated analgesia and sedation could alter sensory perception. Unlike a previous study (Brummett et al. (2008) Anesthesiol. 109:502-51; herein incorporated by reference in its entirety) in which all rats received bilateral sciatic nerve blocks with either bupivacaine alone or bupivacaine plus dexmedetomidine, rats in the present study displayed unilateral blocks with an unblocked control paw, providing an index of systemic analgesia (FIG. 4). The data show that the effects of dexmedetomidine were predominately at the peripheral nerve level (FIG. 4). The highest dose of dexmedetomidine (20 µg/kg) had the greatest systemic effects with significantly longer RoRR (FIG. 6). RoRR times in other dexmedetomidine groups (0.5, 2.0 and 6.0 µg/kg), however, were not significantly different when compared with the ropivacaine control group.

The duration of motor blockade was also increased in the dexmedetomidine groups when compared with ropivacaine (FIG. 5). Median times for return to normal motor function were higher with increasing doses of dexmedetomidine; however, this was only significant with the highest dose of dexmedetomidine (20 µg/kg). Otherwise, there were no significant differences in motor function between the 0.5, 2.0, and 6.0 µg/kg doses of dexmedetomidine.

Clonidine, another $\alpha_2$-adrenoceptor agonist, enhances activity-dependent hyperpolarization by inhibiting the $I_h$ current (Butterworth et al. (1993) Anesth. Analg. 76:295-301; Dalle et al. (2001) Muscle Nerve 24:254-261; Gaumann et al. (1994) Pharmacol. 48:21-29; Starke et al. (1972) Arch. Int. Pharmacodyn. Ther. 195:291-308; each herein incorporated by reference in its entirety). In the central and peripheral nervous systems, the $I_h$ current plays a key role in cell excitability, especially the firing frequency (Pape (1996) Ann. Rev. Physiol. 58:299-327; herein incorporated by reference in its entirety). The $I_h$ current is activated during the hyperpolarization phase of an action potential and normally acts to reset a nerve for subsequent action potentials. Therefore, while the present invention is not limited to any particular mechanism, and an understanding of the mechanism is not necessary to practice the present invention, it is contemplated that by blocking the $I_h$ current, clonidine enhances hyperpolarization and inhibits subsequent action potentials.

The use of dexmedetomidine in the perineural space is not approved by the US Food and Drug Administration and has never been reported in humans. However there was no neurotoxicity noted at 24 hours or 14 days in the seven nerves in the high-dose dexmedetomidine group (20 µg/kg). Experiments conducted during the course of development of some embodiments of the present invention showed no neurotoxicity caused by high-dose dexmedetomidine administered alone or when combined with approved concentrations of bupivacaine in sciatic nerve blocks in rat (Brummett et al. (2008) Anesthesiol. 109:502-51; herein incorporated by reference in its entirety). The combination of dexmedetomidine with bupivacaine was associated with significantly less perineural inflammation at 24 hours when compared with bupivacaine alone (Brummett et al. (2008) *Anesthesiol.* 109: 502-51; herein incorporated by reference in its entirety). While the present invention is not limited to any particular mechanism, and an understanding of the mechanism is not necessary to practice the present invention, these findings were consistent with the anti-inflammatory properties of clonidine found by Eisenach and colleagues (Lavand'homme et al. (2003) *Pain* 105:247-254; Romero-Sandoval et al. (2006) *Anesthesiol.* 104:351-355; Romero-Sandoval et al. (2007) *Brain Behav. Immun.* 21:569-580; Romero-Sandoval et al. (2005) *J. Neurosci.* 25:8988-8994; each herein incorporated by reference in its entirety).

Although ropivacaine and bupivacaine are both long-acting local anesthetics, ropivacaine has unique pharmacologic properties and has replaced bupivacaine for peripheral nerve blocks in many institutions in the United States. The predominate reason for the change is the belief that ropivacaine is more likely to respond to resuscitation efforts in the event of cardiac arrest from intravascular injection when compared with bupivacaine (Chazalon et al. (2003) *anesthesiol.* 99:1449-1451; Khoo et al. (2006) *Anaesth. Intensive Care* 34:804-807; Klein et al. (2003) *Anesth. Analg.* 97:901-903; Polley et al. (2003) *Anesthesiol.* 99:1253-1254; Ohmura et al. (2001) *Anesth. Analg.* 93:743-748; Litz et al. (2006) *Anesthesia* 61:800-801; Hansen (2004) *Expert Rev. Neurother.* 4:781-791; Simpson et al. (2005) *Drugs* 65:2675-2717; each herein incorporated by reference in its entirety). In addition to a safer cardiac profile, some studies have shown that ropivacaine is associated with less motor blockade when compared with bupivacaine (Hansen (2004) *Expert Rev. Neurother.* 4:781-791; Simpson et al. (2005) *Drugs* 65:2675-2717; Dyhre et al. 1997) *Acta Anaesthiol. Scand.* 41:1346-1352; Zink et al. (2004) *Drug Saf.* 27:1093-1114; each herein incorporated by reference in its entirety). Improved motor function while maintaining analgesia allows patients to participate in physical therapy and improves postoperative function. Selectivity for C and A-delta fibers compared with A-alpha fibers has been demonstrated with clonidine (Butterworth et al. (1993) *Anesth. Analg.* 76:295-301; Gaumann et al. (1992) *Anesth. Analg.* 74:719-725; each herein incorporated by reference in its entirety).

Dexmedetomidine added to ropivacaine increased the duration of sensory blockade to a heat stimulus in rat in a dose-dependent fashion. Increasing doses of dexmedetomidine were associated with longer times of dense sensory blockade and time to return of normal sensory function. Nociceptive testing of the control paw revealed no significant change in PWL caused by dexmedetomidine. This finding supports the interpretation that the analgesic effects of dexmedetomidine on the operated paw resulted from actions at the level of the sciatic nerve.

Example 3

Perineural Dexmedetomidine Provides an Increased Duration of Analgesia to a Thermal Stimulus when Compared to a Systemic Control in a Rat Sciatic Nerve Block Since perineural dexmedatomidine (20 µg/kg) was associated with delayed resumption of righting response in rats (Example 2), the potential for dexmedetomidine-induced sedation effects on sensory assessment was analyzed. An experiment was conducted to determine whether perineural dexmedetomidine would significantly increase the duration of a sciatic peripheral nerve block in rats when compared with the same dose administered subcutaneously. Secondary analyses included the analgesic effects of perineural and systemic dexmedetomidine alone.

Methods

Methods were as described in Example 1, with the following exceptions. A total of 54 Sprague-Dawley rats weighing 250-350 g were used. Animal care and handling was conducted as described in Example 1. Drugs were prepared as described in Example 1. The five treatment groups described in Table 3 differed in the composition of both the drug injected in the perineural space near the sciatic nerve and in the subcutaneous injection. Rats were assigned to the treatment group using random sampling without replacement. Each rat received a 0.2 ml perineural sciatic injection and a 0.2 ml subcutaneous injection. All doses of dexmedetomidine were based on the weight of each individual rat for 20.0 µg/kg with final mean concentrations of 119.3±4.5 µM. Subfascial sciatic nerve injections were performed as described in Example 1. Immediately following the perineural injection, 0.2 ml of drug was injected subcutaneously in the fold of skin at the back of the neck. The muscle and skin of the thigh were sutured, and the isoflurane was discontinued.

TABLE 3

Study groups. All rats were randomized to one of five groups to receive a 0.2 ml perineural injection of study drug, along with a 0.2 ml subcutaneous injection under the fold of skin at the base of the neck. All final concentrations of ropivacaine were maintained at 0.5%, and dexmedetomidine (DEX) were all dosed at 20.0 µg/kg (119.3 ± 4.5 µM).

| Group | Perineural injection (0.2 ml) | Subcutaneous injection (0.2 ml) |
| --- | --- | --- |
| Group 1 | Ropivacaine | Saline |
| Group 2 | Ropivacaine + DEX | Saline |
| Group 3 | Ropivacaine | DEX |
| Group 4 | DEX | Saline |
| Group 5 | Saline | DEX |

Neurobehavorial examination and PWL testing was conducted as described in Example 1, with the exception that the minimum monitoring period was 240 minutes. The relative systemic versus peripheral perineural effects of dexmedetomidine were determined by observing the PWL for the blocked and unblocked (control) paw. The effect of sensory analgesia (as measured by the PWL) to the operative paw compared with the control paw was calculated and is reported as the inter-paw differential (IPD=100*[Operative PWL–Control PWL]/Control PWL). Therefore, an IPD of 0% indicates that the response to a thermal stimulus was equivalent between the blocked and unblocked paws, while an IPD of 100% indicates that the operative PWL was twice as long as the control paw. The IPD is a measure of relative effect and does not describe the quantitative sensory response.

Data were analyzed using SAS 9.2 (SAS Institute Inc., Cary, N.C.) and GraphPad Prism 5.0a (GraphPad Software Inc., La Jolla, Calif.). IPD data were analyzed using a two way repeated measures analysis of variance. Post hoc tests were used to compare IPD between the different drug doses at individual time points. Because some of the rats had a return of normal sensory and motor function at or before 240 minutes, individual time points beyond 240 minutes were not analyzed between groups. For the between group comparisons of the ropivacaine alone, ropivacaine plus perineural dexmedetomidine, and ropivacaine plus subcutaneous dexmedetomidine, a Bonferroni correction for multiple comparisons was used ($\alpha=0.017$ for each comparison). For the comparisons between the operative and control paws and between perineural dexmedetomidine alone and subcutaneous dexmedetomidine alone, a P value of 0.05 was deemed significant. Data are presented as mean±SEM. RoRR, mean isoflurane concentration, and surgery duration data were analyzed using repeated measures one-way analysis of variance with a Tukey's post hoc analysis.

Results

Figure 7:
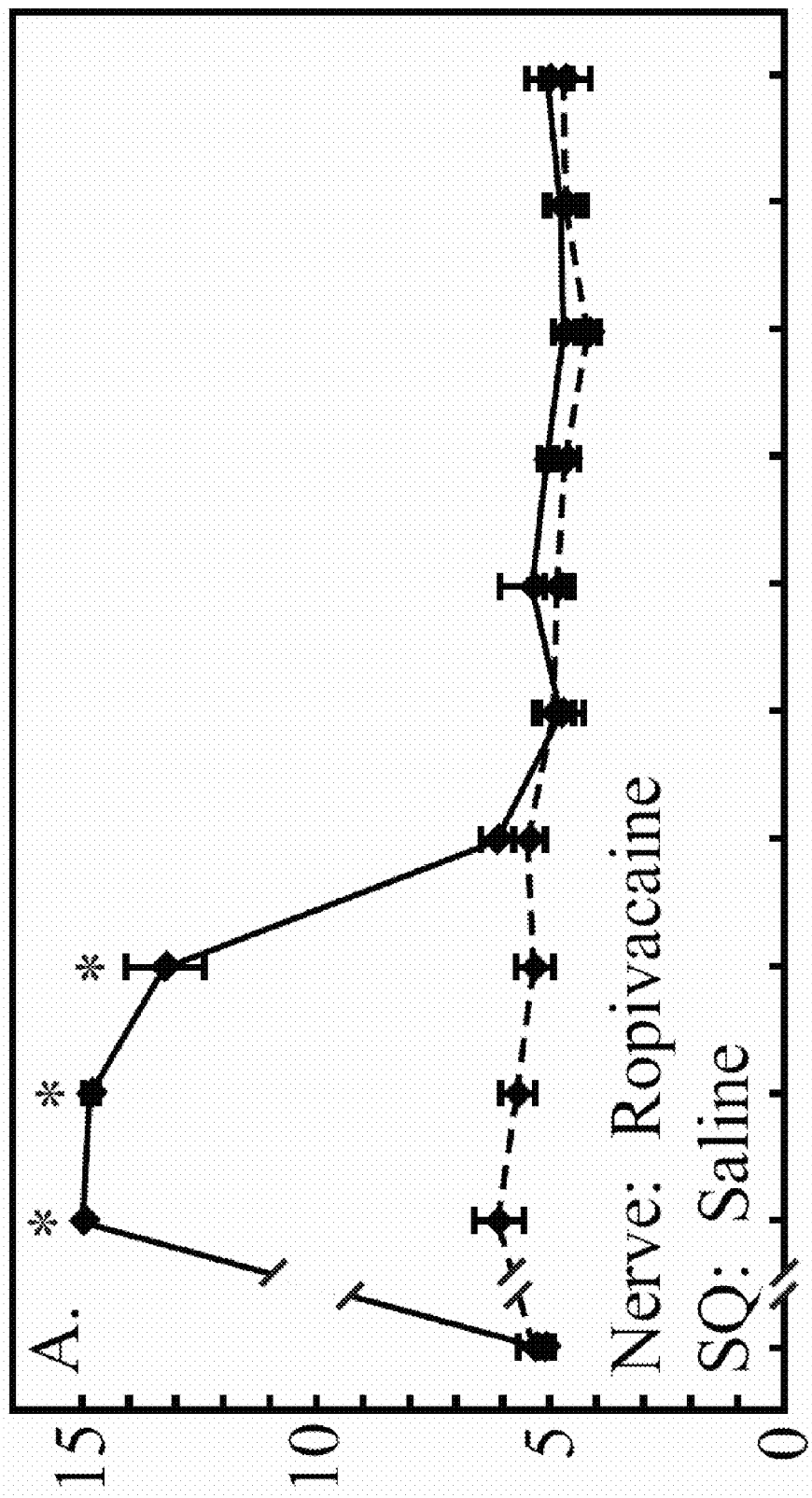
FIG. 7 shows a comparison of operative versus control paw data. The paw withdrawal latency (PWL) to a thermal stimulus of the operative paw (solid line) versus the unblocked, control paw (dashed line) at the 30-minute time points from the baseline measurements (BL) to 300 minutes following the nerve block were compared at every time point for each of the five groups. The greatest effect between the paws was seen when perineural dexmedetomidine was added to ropivacaine for the nerve block (FIG. 7B). Dexmedetomidine did provide a short, partial blockade of the operative paw (FIG. 7D). The groups in which dexmedetomidine was administered subcutaneously demonstrated more effect on the unblocked control paw when compared to the same combination delivered perineurally (FIG. 7B versus 7C.
Figure 7:
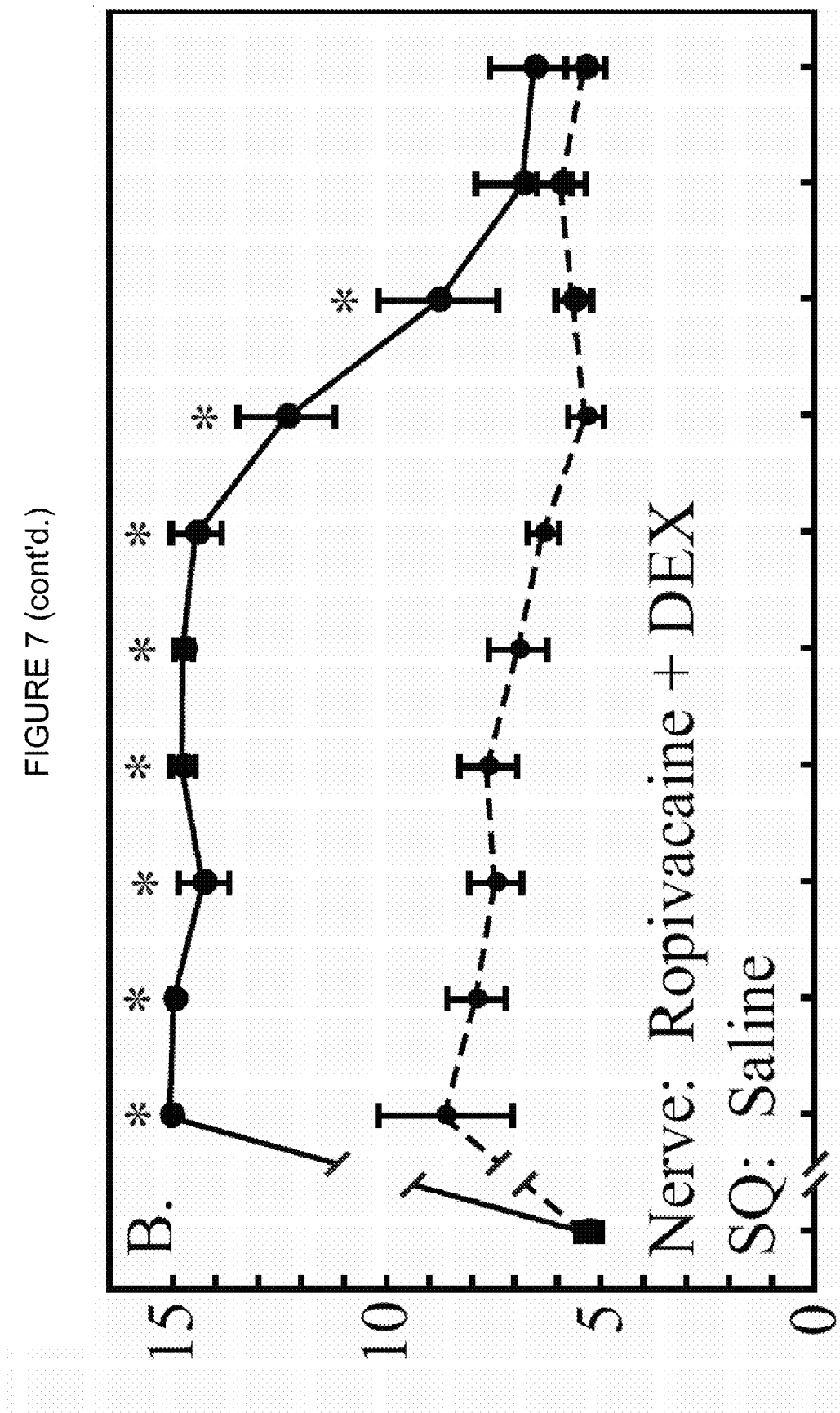
Figure 7:
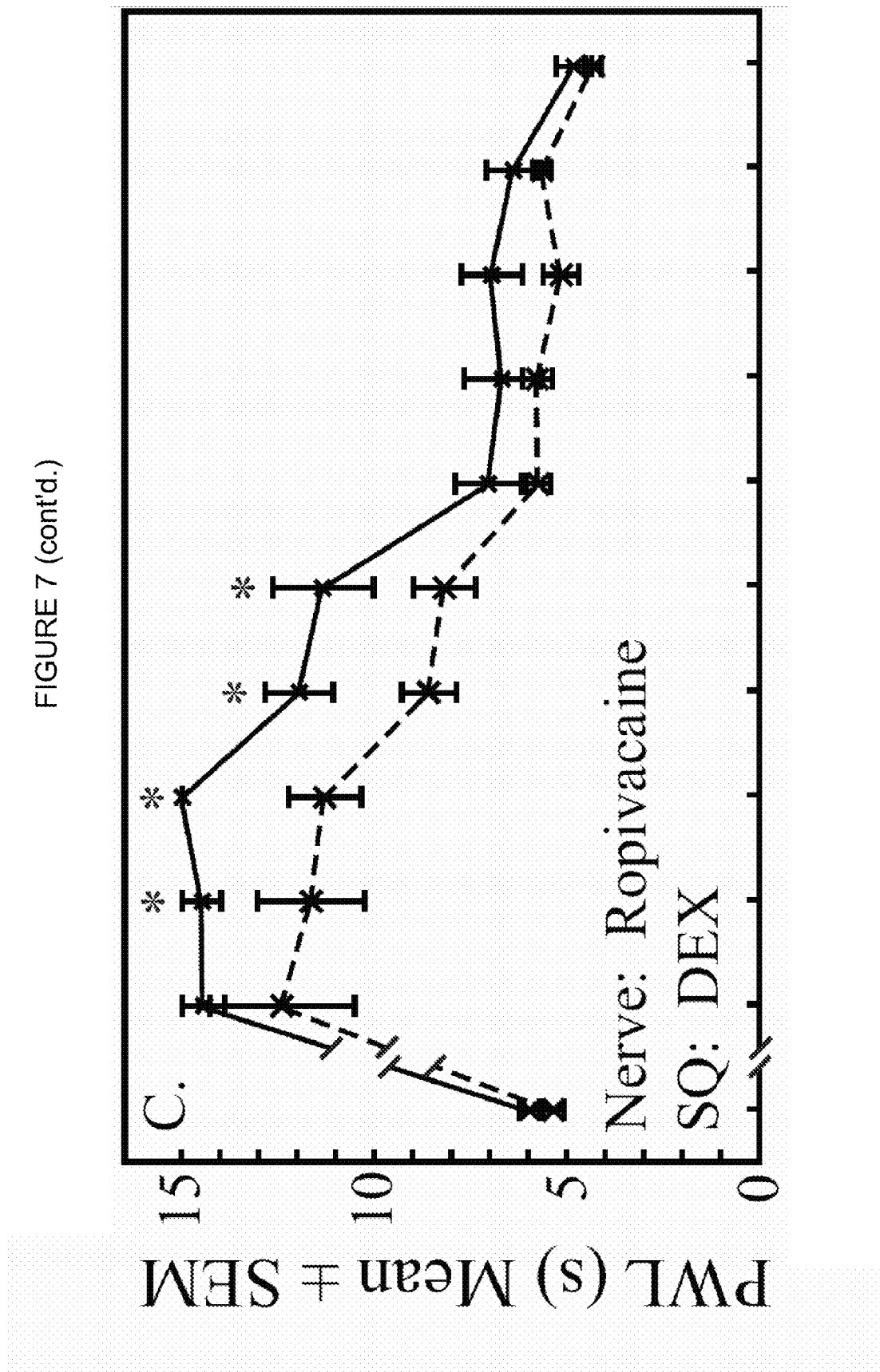
Figure 7:
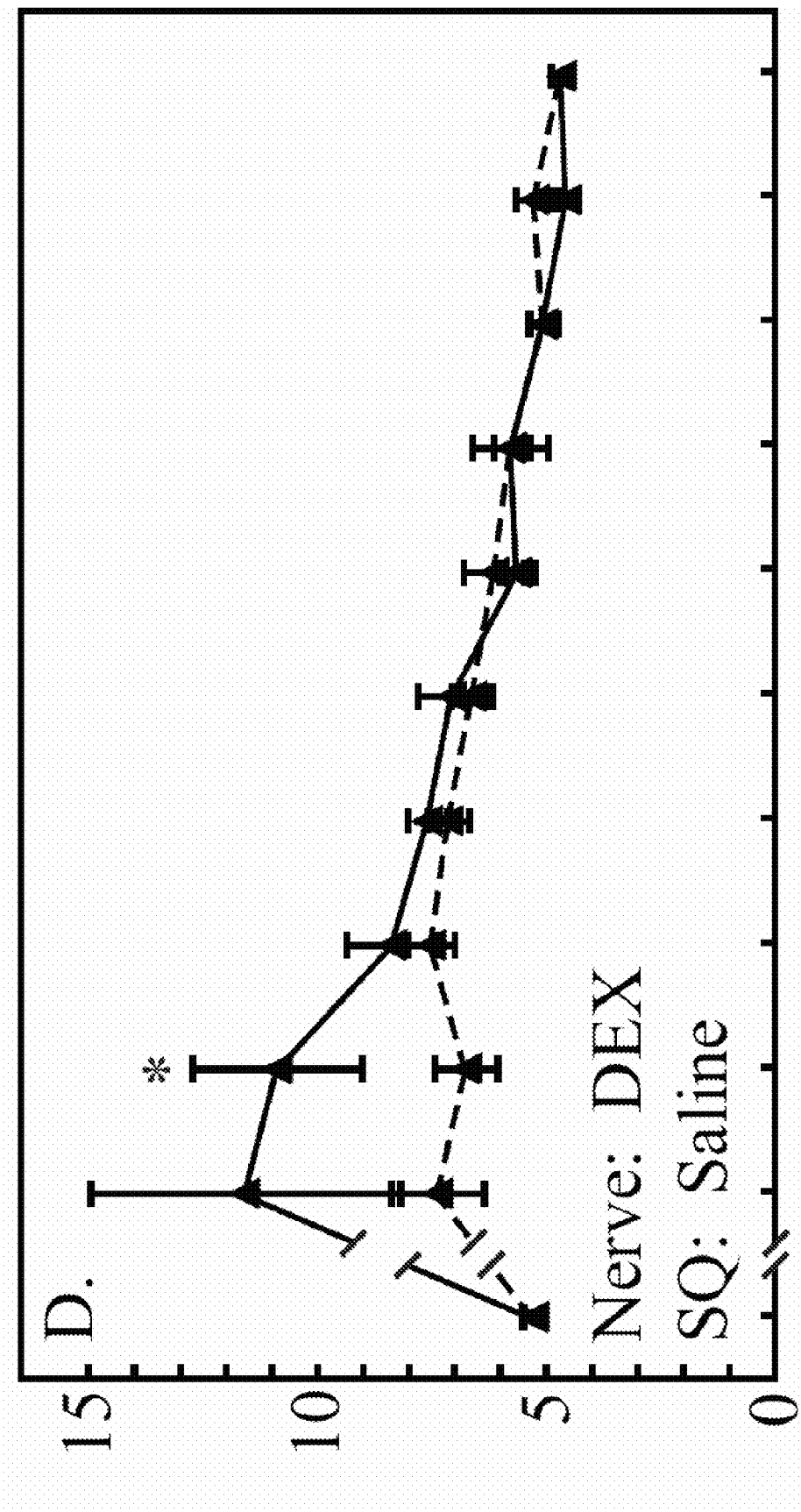
Figure 7:
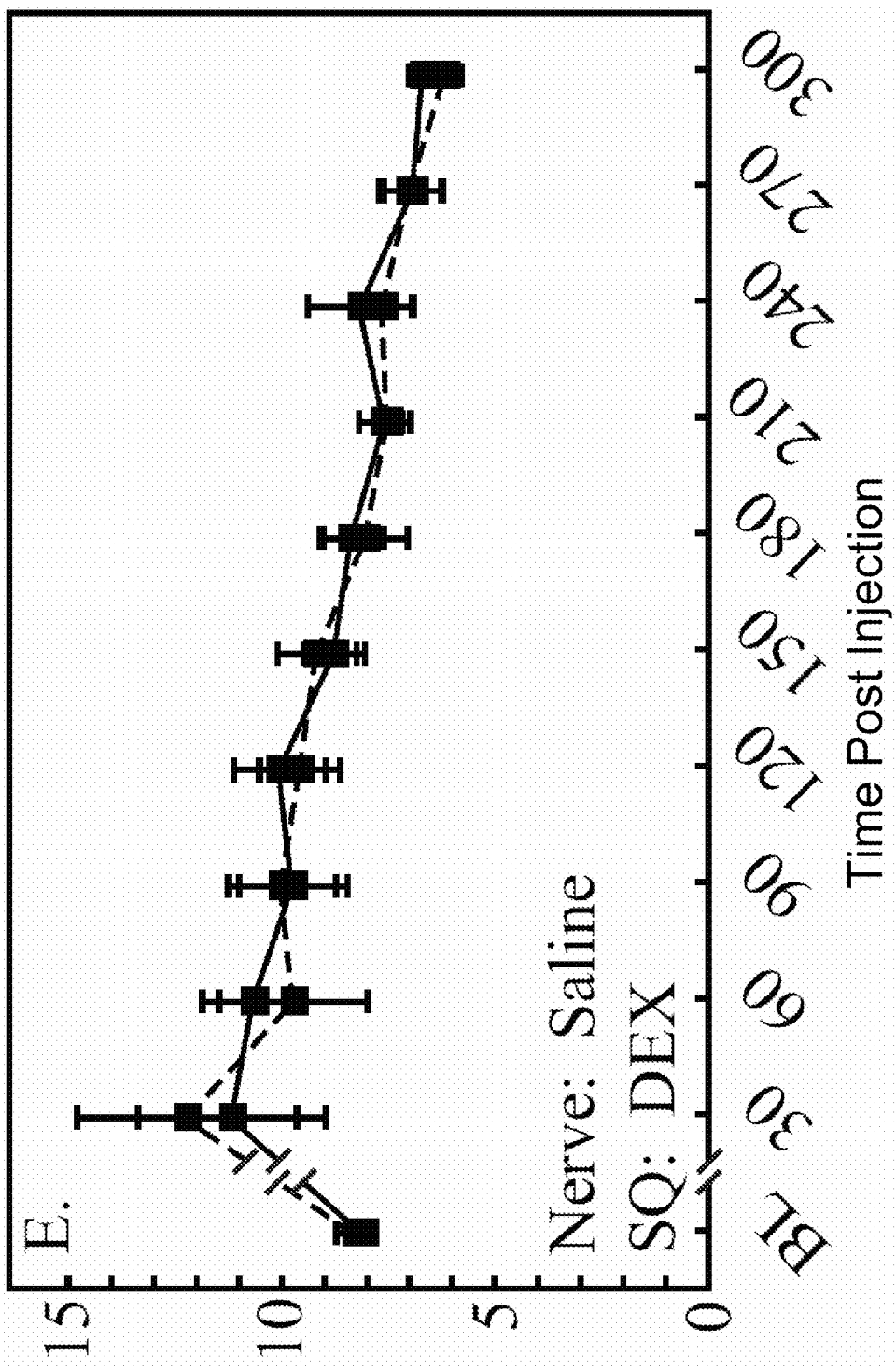

Perineural and subcutaneous high-dose dexmedetomidine co-administered with perineural ropivacaine enhanced, the duration of sensory blockade when compared with ropivacaine alone (FIG. 7A-C). There were significant differences between the operative and control paws (p<0.05) for time points 30-90 minutes in the ropivacaine alone group (FIG. 7A). Significant differences were noted between the operative and control paw from 30-240 minutes when dexmedetomidine was added to the perineural ropivacaine solution (FIG. 7B, p<0.05 at each time point), while the same dose of dexmedetomidine given subcutaneously with a perineural ropivacaine block only showed a difference from 60-150 minutes (FIG. 7C).

The effects of high-dose dexmedetomidine alone given perineurally and systemically were also evaluated. The analgesic effect of dexmedetomidine alone was not as great as when it was coadministered with ropivacaine or when compared with ropivacaine alone. Perineural dexmedetomidine alone provided a brief, partial sensory blockade, as demonstrated by the difference between the operative and control paws at 60 minutes (FIG. 7D, p=0.001), while the same dose given alone subcutaneously affected both paws equally (FIG. 7E).

Figure 8:
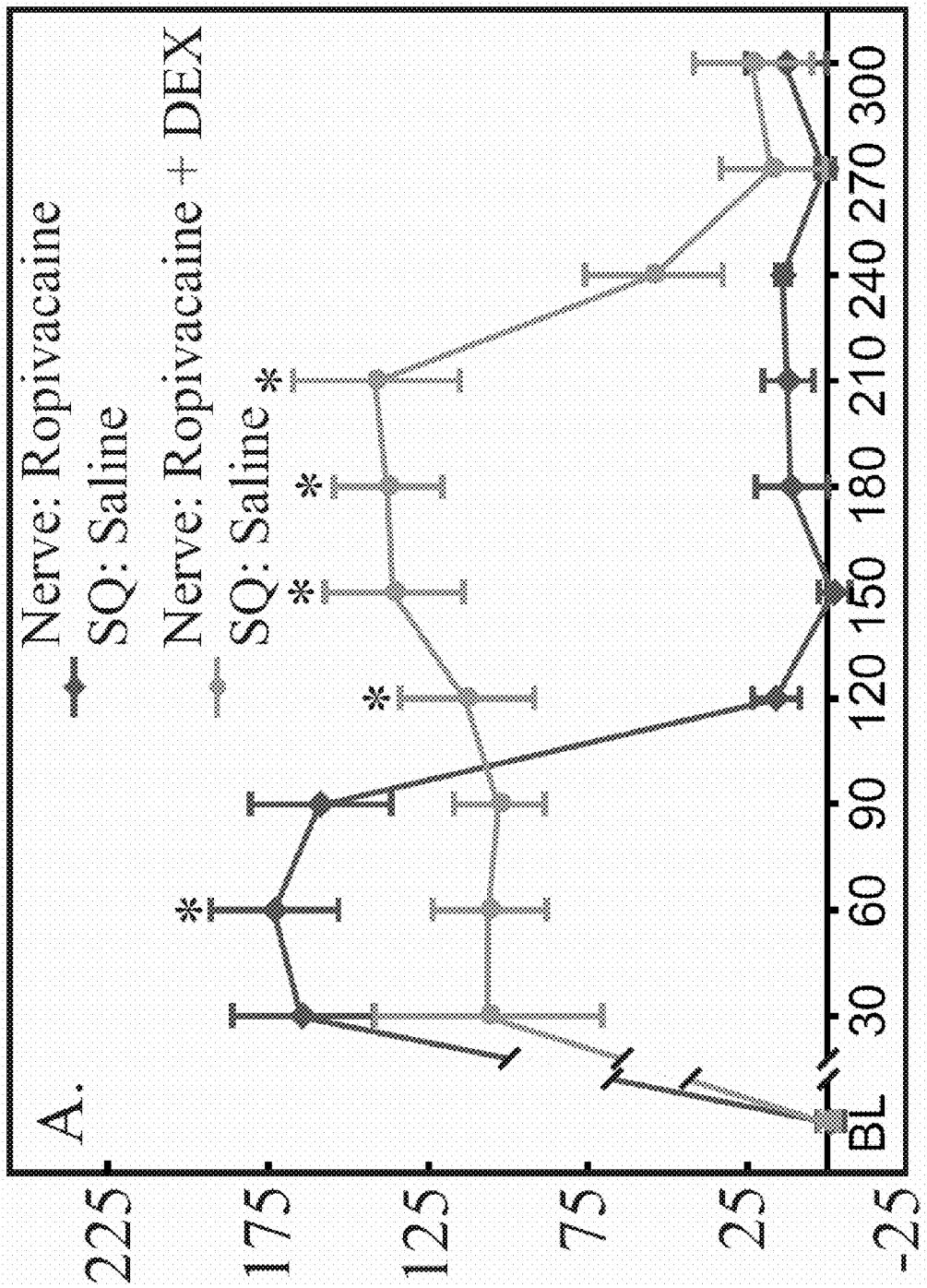
FIG. 8 shows inter-paw differential for dexmedetomidine added to ropivacaine. The relative effect of the operative versus the control paw was compared between the three ropivacaine groups at each time point. After the resolution of the sensory blockade in the ropivacaine alone group at 120 minutes, the addition of perineural dexmedetomidine increased the duration of the inter-paw differential (FIG. 8A). The same dose of dexmedetomidine administered subcutaneously also increased the duration of the relative blockade when compared to ropivacaine alone at time point 150 min (FIG. 8B); however, the effect was not as sustained as when compared with the perineural dexmedetomidine group (FIG. 8C). The drug condition for each group is noted in the top right corner (Nerve=drug injected perineurally; SQ=drug injected subcutaneously). BL=baseline measurement; DEX=dexmedetomidine; * indicates statistically significant result ($P<0.017$).
Figure 8:
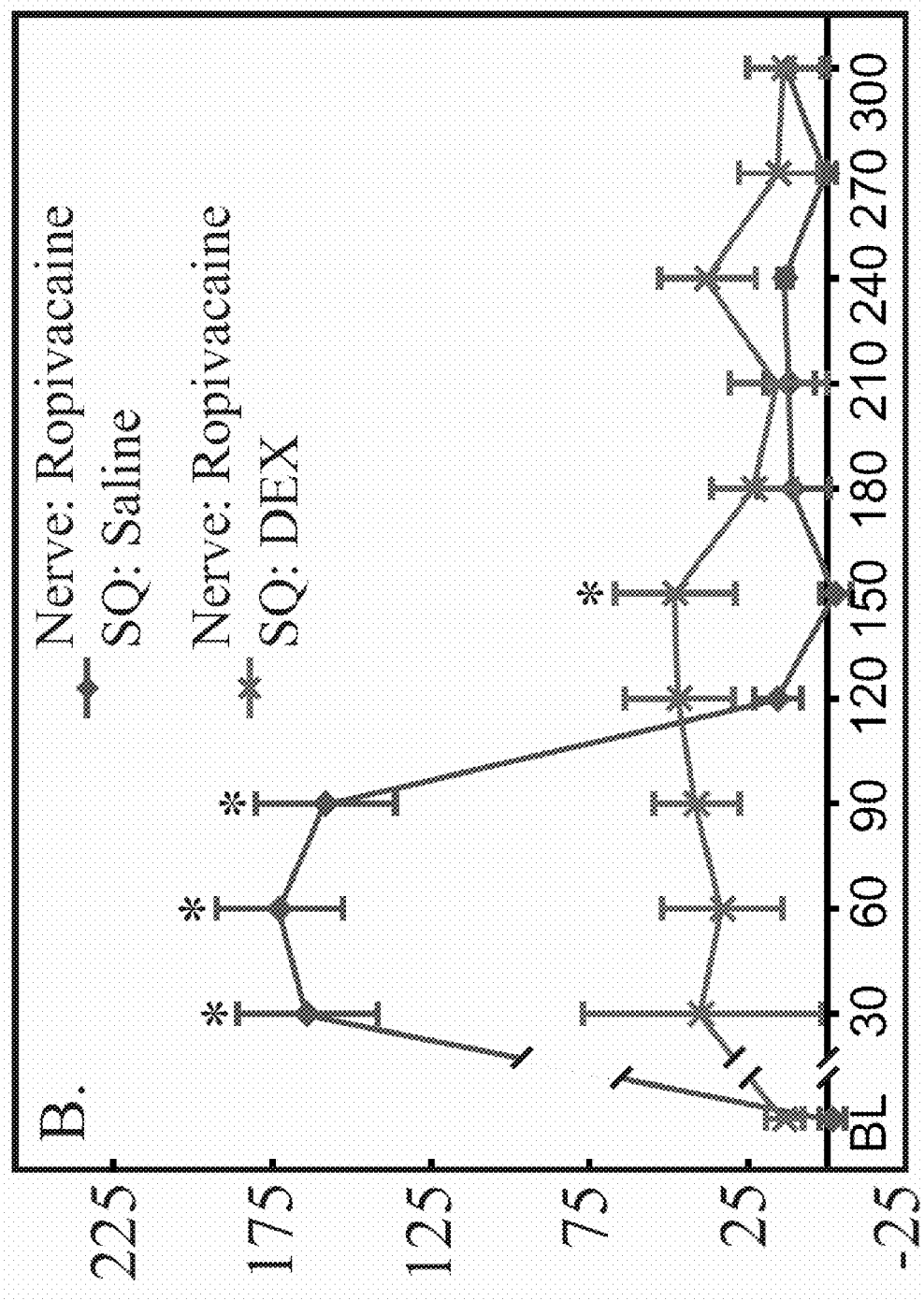
Figure 8:
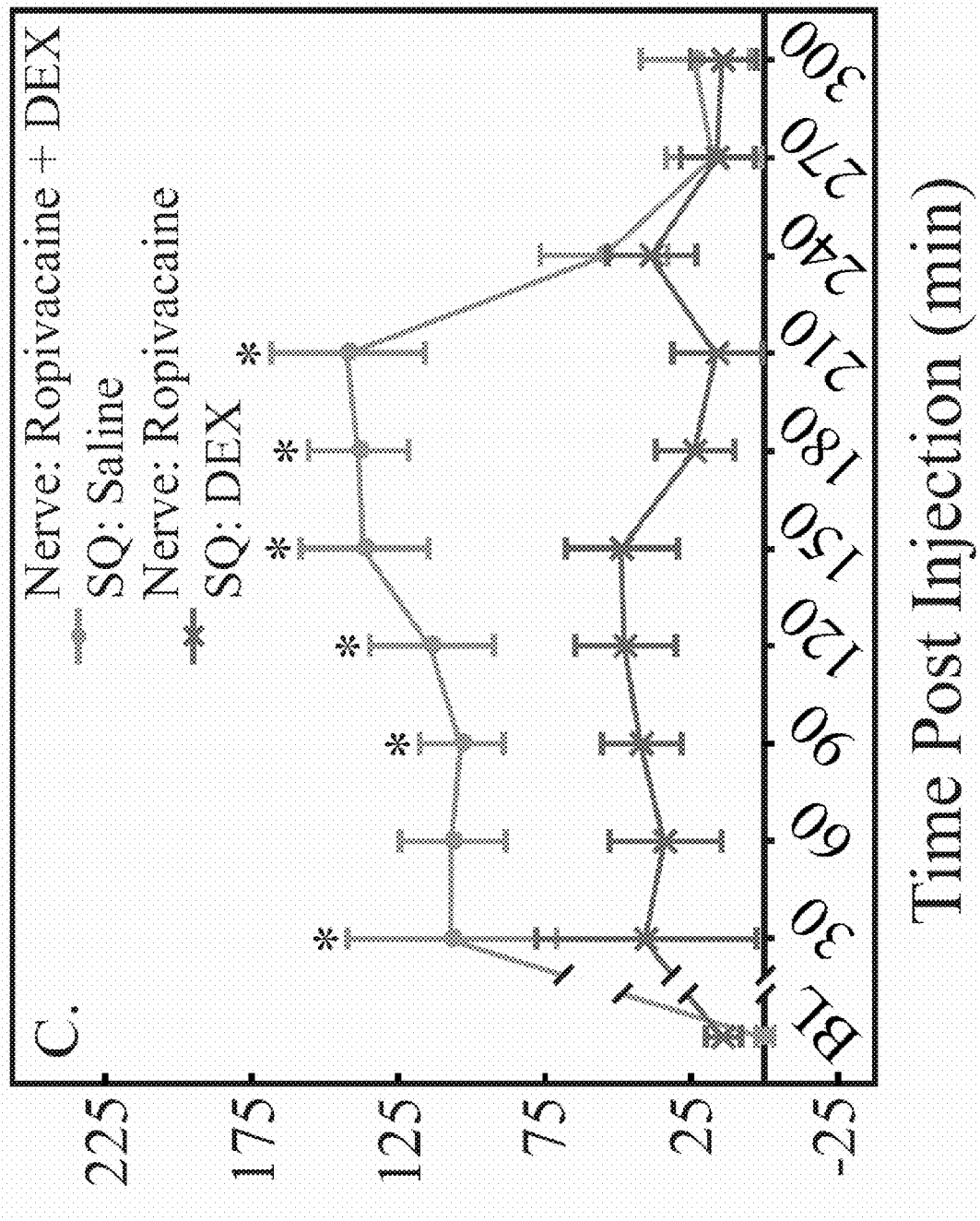

The relative systemic versus peripheral perineural effects of dexmedetomidine were determined by observing the PWL for the blocked and unblocked (control) paw from 0-240 minutes (Inter-paw differential [IPD]; see Methods supra for details and calculation). Perineural dexmedetomidine added to ropivacaine produced a greater relative sensory analgesic effect to the operative paw when compared with the other two groups at time points 120-210 minutes (p<0.017; FIGS. 8A and 8C). The relative effect of the same dose of dexmedetomidine given subcutaneously compared with ropivacaine alone was only significantly greater at the 150-minute time point (p=0.0006; FIG. 8B).

Ropivacaine alone had a greater relative effect on the blocked paw for the first 90 minutes due to the systemic effects on the control paw of dexmedetomidine (FIG. 8A-B). During the 30-90 min time points, the ropivacaine alone, ropivacaine with perineural dexmedetomidine, and ropivacaine with subcutaneous dexmedetomidine groups all exhibited dense blockade of the operative paws with PWL scores at or near the cutoff threshold of 15 s (FIG. 7A-C).

Figure 9:
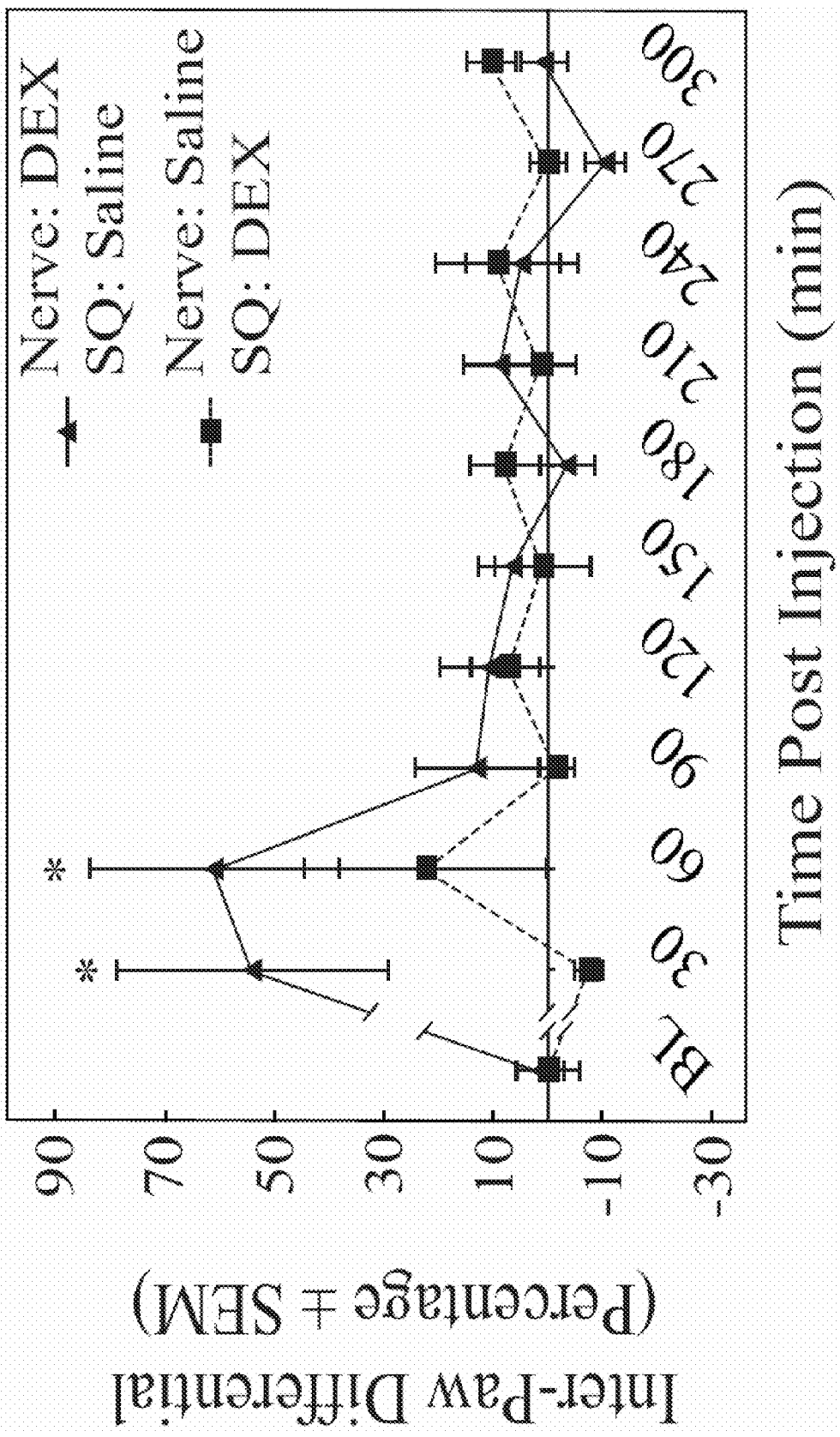
FIG. 9 shows inter-paw differential for perineural versus subcutaneous dexmedetomidine. Perineural high-dose dexmedetomidine (solid line) provided a short sensory blockade, which was not seen with the same dose given subcutaneously (dashed line). There were no significant differences between the operative and control paws at any time point for the subcutaneous dexmedetomidine group. The drug condition for each group is noted in the top right corner (Nerve=drug injected perineurally; SQ=drug injected subcutaneously). DEX=dexmedetomidine; $P<0.05$ deemed statistically significant.

The relative effect of perineural dexmedetomidine alone was greater than subcutaneous dexmedetomidine alone. At time points 30- and 60-minutes perineural dexmedetomidine was significantly different compared to systemic administration (FIG. 9, p=0.006 and 0.002, respectively). The local anesthetic-like action was not as great as when dexmedetomidine was co-administered with ropivacaine or compared with ropivacaine alone (FIG. 8), but it was significantly greater than systemic administration.

The RoRR was significantly longer in the ropivacaine plus subcutaneous dexmedetomidine group when compared with ropivacaine alone (38.6±13.3 versus 5.5±0.8 minutes, respectively; p=0.02). There were no differences when these groups were compared with ropivacaine plus perineural dexmedetomidine (26.1±5.8 minutes). There were also no differences in RoRR between perineural dexmedetomidine alone (55.1±7.8 minutes) versus subcutaneous dexmedetomidine alone (53.9±11.4 minutes). There were no significant differences between groups for duration of surgery or isoflurane levels. Neurobehavioral monitoring 24 h after the nerve blocks showed no significant differences in PWL between the operative paws of the five groups or between the operative and control paws. In addition, there were no noted gross motor deficits.

Perineural dexmedetomidine added to ropivacaine significantly increased the duration of sensory blockade, along with a lesser systemic effect as measured by the control paw, when compared to the systemic (subcutaneous) control dexmedetomidine group (FIGS. 7A-C and 8A-C). Dexmedetomidine significantly increased the duration of sensory analgesia when compared with ropivacaine alone. The addition of systemic (subcutaneous) dexmedetomidine increased the duration of analgesia when compared to ropivacaine alone, but the duration of increase was not as prolonged as the same concentration of dexmedetomidine administered perineurally. In addition, the systemic dexmedetomidine group had a greater analgesic effect on the unblocked control paw (FIGS. 7C and 8C), thereby indicating that the effects of perineural dexmedetomidine (Brummet et al. (2008) Anesthesiool. 109:502-511; herein incorporated by reference) (Example 2) are not due to centrally mediated sedation or analgesia.

High-concentration perineural dexmedetomidine without local anesthetic did provide a short duration sensory blockade (FIGS. 7D and 9). The relative effect of the operative to non-operative paw was significantly greater with perineural versus systemic dexmedetomidine. Clonidine is known to inhibit C- and A∝-fiber conduction in a concentration-dependent manner (Dalle et al. (2001) Muscle Nerve 24:254-261; Gaumann et al. (1994) Pharmacol. 48:21-29; Butterworth et al. (1993) Anesth. Analg. 76:295-301; Gaumann et al. (1992) Anesth. Analg. 74:719-725; each herein incorporated by reference in its entirety). The use of perineural clonidine alone in humans, however, did not provide significant analgesia, likely due to limits of the concentration of clonidine used due to side effects (Sia et al. (1999) Anesth. Analg. 88:1109-1112; herein incorporated by reference in its entirety). When administered as a pretreatment through an interscalene catheter prior to postoperative patient-controlled analgesia using 0.2% ropivacaine, perineural clonidine significantly improved initial pain scores, ropivacaine consumption, analgesic consumption, and analgesic duration when compared with the same dose of clonidine administered subcutaneously (Iskandar et al. (2003) Anesth. Analg. 96:260-262; herein incorporated by reference in its entirety). Both oral and intrathecal clonidine enhance the duration of analgesia from a bupivacaine spinal anesthetic (Dobrydnjov et al. (2002) Anaesthiol. Scand. 46:806-814; Ota et al. (1992) Anesth. Analg. 75:262-264; each herein incorporated by reference in its entirety). A clinical study demonstrated that the effect of perineural clonidine with local anesthetic for brachial plexus blockade was superior to an intramuscular clonidine control (Hutschala et al. (2004) Eur. J. Anaesthesiol. 21:198-204; herein incorporated by reference in its entirety).

Rats in the dexmedetomidine groups had longer RoRR times when compared with the group that received ropivacaine alone. The concentration of dexmedetomidine was the same throughout the groups, with the only differences being the route of administration (perineural or subcutaneous) and the other drugs administered perineurally (ropivacaine or normal saline). Dexmedetomidine causes centrally mediated sedation and analgesia (Carollo et al. (2008) Curr. Opin. Anaesthesiol. 21:457-461; herein incorporated by reference in its entirety). Peripheral perineural clonidine enhances postoperative analgesia through an activity-dependent inhibition of the inwardly-rectifying potassium current (In current), not through the $\alpha_2$-adrenoceptor (Dalle et al. (2001) Muscle Nerve 24:254-261; Kroin et al. (2004) Anesthesiol. 101:488-494; each herein incorporated by reference in its entirety). Peripheral administration of clonidine has been demonstrated to decrease peripheral perineural inflammation, which is an $\alpha_2$-mediated effect (Lavand'homme et al. (2003) Pain 105: 247-254; Lavand'homme et al. (2002) Anesthesiol. 97:972-980; Liu et al (2006) Neuroreport 17:1313-1317; Romoero-Sandoval et al. (2006) Aneesthesiol. 104:351-355; each herein incorporated by reference in its entirety). The analgesic properties of intrathecal clonidine are mediated via the $\alpha_2$-adrenoceptor (Yaksh et al. (1995) J. Pharmacol. Exp. Ther. 272:207-214; herein incorporated by reference in its entirety).

While the present invention is not limited to any particular mechanism, and an understanding of the mechanism is not necessary to practice the present invention, it is contemplated that dexmedetomidine increases the duration of analgesia to a thermal stimulus through a peripheral perineural mechanism in a rat sciatic nerve block model. The administration of equivalent systemic doses of dexmedetomidine increases the postoperative sedation and analgesia to the unblocked paw without providing the same duration of analgesia.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A method for reducing pain in a human subject, comprising perineurally administering 5 µg/kg or less dexmedetomidine in combination with ropivacaine as a peripheral nerve block.

2. The method of claim 1, wherein the dose of ropivacaine is 1.0% or less.

3. The method of claim 1, wherein said human subject has an additional condition selected from the group consisting of advanced age, neonatal status, pediatric status, impaired pulmonary function, impaired liver function, impaired cardiovascular function, impaired metabolic function, impaired renal function, impaired gastrointestinal function, impaired neuromuscular function, pregnancy, diabetes, impaired cognitive function, and impaired tolerance of anesthetic or analgesic agents.

4. The method of claim 1, wherein the type of said peripheral nerve block is selected from the group consisting of a motor nerve block, a sensory nerve block, a differential nerve block, an autonomic nerve block, a brachial plexus nerve block (axillary, interscalene, supraclavicular, infraclavicular), an individual upper extremity nerve block (median, radial, ulnar, musculocutaneous, axillary), a sciatic nerve block, an ankle nerve block, a metatarsal nerve block, an oral nerve block, a femoral nerve block, a popliteal fossa nerve block, a saphenous nerve block, a distal nerve block, a digital nerve block, a deep peroneal nerve block, a superficial peroneal nerve block, a tibial nerve block, a sural nerve block, and a saphenous nerve block.

5. The method of claim 1, wherein the delivery route is selected from the group consisting of single injection, serial injections, indwelling catheter, continuous infusion, transdermal administration, and transmucosal administration.

6. The method of claim 1, wherein the type of said pain is selected from the group consisting of acute pain, chronic pain, thermal pain, traumatic pain, chemical pain, inflammatory pain, ischemic pain, blunt pain, sharp pain, prickling pain, visceral pain, and neuropathic pain.

* * * * *